US007956758B2

(12) United States Patent
    Hattori

(10) Patent No.: US 7,956,758 B2
(45) Date of Patent: Jun. 7, 2011

(54) THERMAL STIMULATION APPARATUS FOR VEHICLES

(75) Inventor: Koji Hattori, Toyota (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 483 days.

(21) Appl. No.: 12/278,588

(22) PCT Filed: Feb. 6, 2007

(86) PCT No.: PCT/JP2007/051976
§ 371 (c)(1),
(2), (4) Date: Aug. 7, 2008

(87) PCT Pub. No.: WO2007/091538
PCT Pub. Date: Aug. 16, 2007

(65) Prior Publication Data
US 2009/0040055 A1    Feb. 12, 2009

(30) Foreign Application Priority Data

Feb. 8, 2006   (JP) .................................. 2006-030891

(51) Int. Cl.
    *G08B 23/00* (2006.01)
(52) U.S. Cl. ........ 340/576; 340/581; 340/584; 180/271; 280/735
(58) Field of Classification Search .................. 340/584, 340/581, 575, 576; 280/734, 735; 180/271, 180/272
See application file for complete search history.

(56) References Cited

U.S. PATENT DOCUMENTS

| 6,043,743 A *     | 3/2000  | Saito et al. ..................... 340/562 |
| 2004/0201481 A1 * | 10/2004 | Yoshinori et al. ............. 340/575 |

FOREIGN PATENT DOCUMENTS

| EP | 1 116 611    | 7/2001  |
| FR | 2 802 470    | 6/2001  |
| JP | 55-156976    | 12/1980 |
| JP | 60-83670     | 5/1985  |
| JP | 64-67886     | 3/1989  |
| JP | 4-269972     | 9/1992  |
| JP | 07-275363    | 10/1995 |
| JP | 2002-250532  | 9/2002  |

(Continued)

OTHER PUBLICATIONS

K. Nishijo, "Bioresponse to Acupuncture and the Autonomic Nerve," Scientific Perspective, vol. 40, No. 1, p. 26 (Feb. 15, 2003).

(Continued)

*Primary Examiner* — Hung T. Nguyen
(74) *Attorney, Agent, or Firm* — Finnegan, Henderson, Farabow, Garrett & Dunner, LLP

(57) ABSTRACT

A thermal stimulation apparatus for vehicles capable of exerting an effect of, for example, reducing fatigue and improving the physical condition of a vehicle occupant. In a vehicle thermal stimulation apparatus 10, the piezoelectric sensor 26 detects a biorhythm accompanying a periodic change in an occupant, a control circuit 16 switches on and off heater elements 22, 24 on the basis of the detection result of the biorhythm detector such that by the heater elements 22, 24 being switched on and off, thermal stimulus to the occupant is synchronized with the biorhythm of the occupant. It is thereby possible to exert effects of, for example, reducing fatigue and improving the physical condition of a vehicle occupant.

11 Claims, 17 Drawing Sheets

FOREIGN PATENT DOCUMENTS

| | | |
|---|---|---|
| JP | 2003-332030 | 11/2003 |
| JP | 2004-283403 | 10/2004 |
| JP | 2004-290499 | 10/2004 |
| JP | 2004-329611 | 11/2004 |
| KR | 2001-0065596 | 7/2001 |

OTHER PUBLICATIONS

Extended European Search Report for EP 07708094.3 dated Mar. 4, 2010.

Japanese Office Action dated May 19, 2009.

* cited by examiner

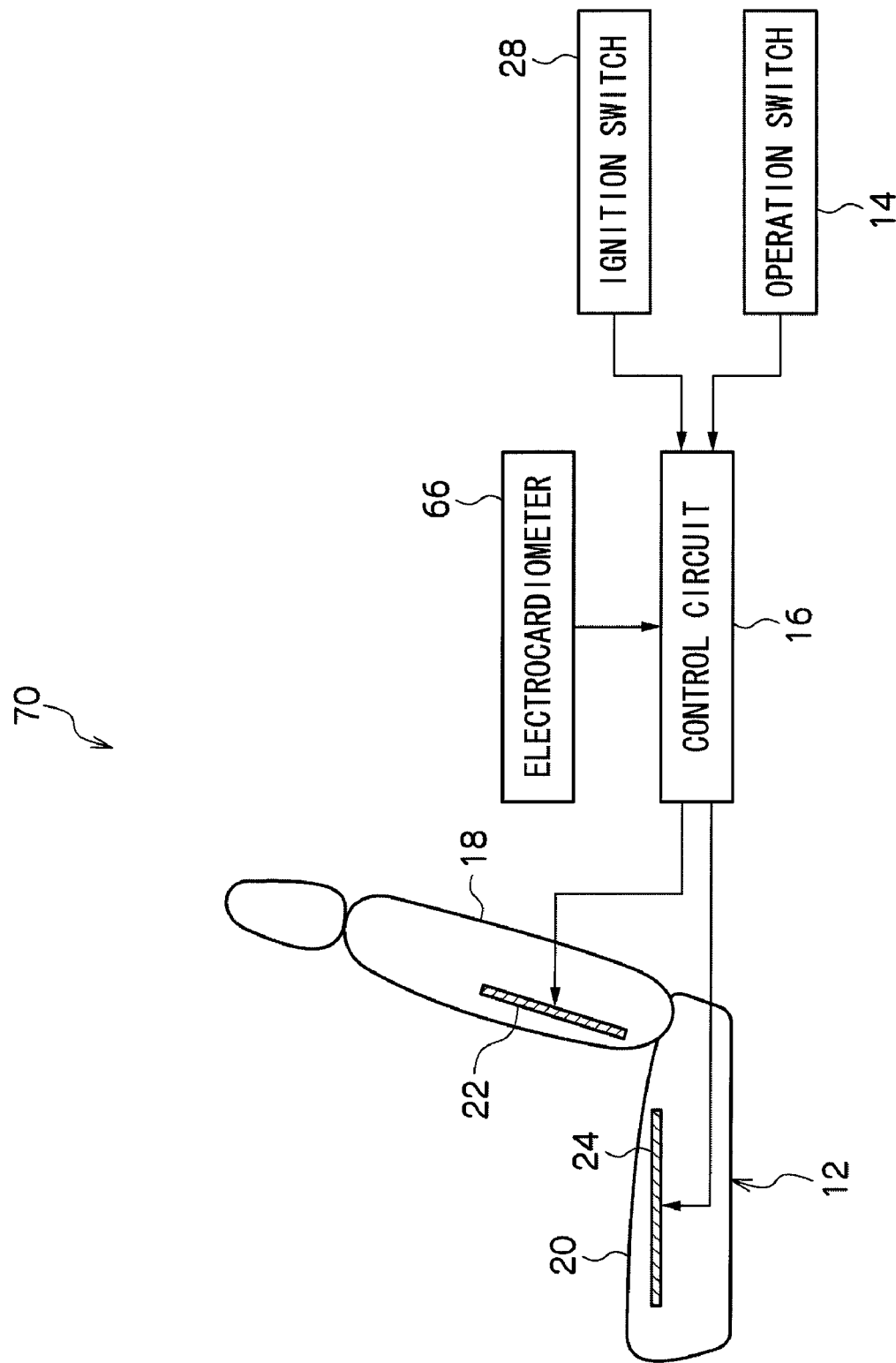

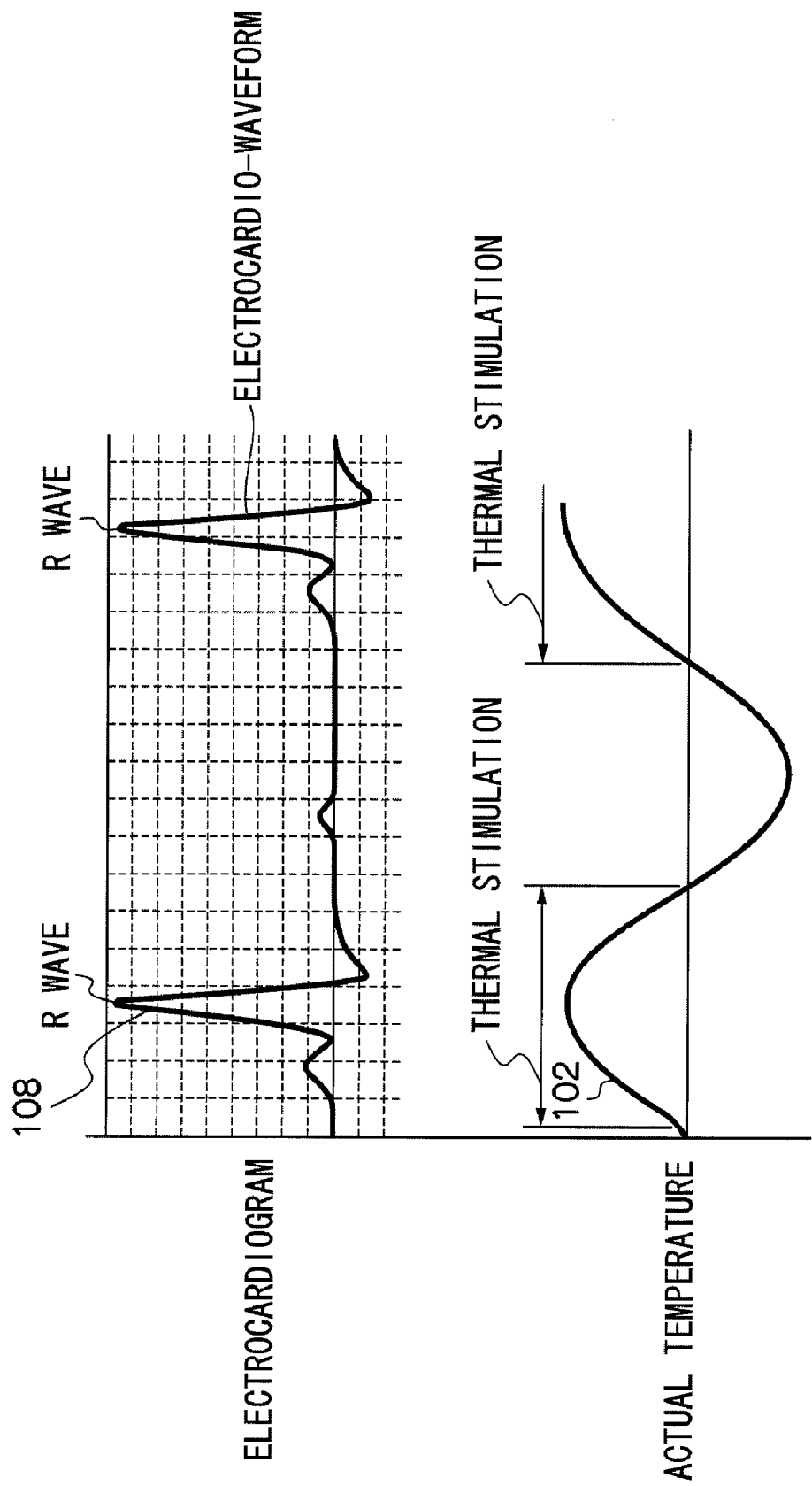

THERMAL STIMULATION APPARATUS FOR VEHICLES

CROSS-REFERENCE TO RELATED APPLICATIONS

This application is a national phase application of International Application No. PCT/JP2007/051976, filed Feb. 6, 2007, and claims the priority of Japanese Application No. 2006-030891, filed Feb. 8, 2006, the contents of both of which are incorporated herein by reference.

TECHNICAL FIELD

The present invention relates to a thermal stimulation apparatus for vehicles, and in particular to a vehicle thermal stimulation apparatus capable of applying thermal stimulus to an occupant of a vehicle.

RELATED ART

The following types of heating apparatus are conventionally known (see, for example, Patent Document 1 and Patent Document 2). An example of a seat heater for a vehicle is described, for example in Patent Document 1. The example described in Patent Document 1 is a vehicle seat provided with plural heaters, divided up such that the amount of heat generated from the plural heaters can be varied. A high-speed heating sensation is given to a seated occupant by concentrating the heating to regions where a warm sensation is readily felt by a person's body.

Further, for example in the Patent Document 2, an example of an electrical carpet is also described. In the example described in Patent Document 2 the respiration rate and the pulse rate of the user are measured, and a heater is adjusted by raising or lowering the temperature thereof in accordance with increases and decreases in the respiration rate and pulse rate.

Patent Document 1: Japanese Patent Application Laid-Open (JP-A) No. 2003-332020 (FIGS. 1 and 2)
Patent Document 2: JP-A No. 2002-250532 (FIG. 12)
Patent Document 3: JP-A No. 64-67886

DISCLOSURE OF THE INVENTION

Problem to be Solved by the Invention

The examples described in Patent Document 1 and Patent Document 2, however, do not consider exerting effects of, for example, reducing fatigue and improving the physical conditions of a vehicle occupant by applying thermal stimulus to the vehicle occupant. There is, accordingly, room for improvement in exerting an effect of, for example, reducing fatigue and improving the physical condition of a vehicle occupant.

The present invention is made in consideration of the above, and an objective thereof is to provide a vehicle thermal stimulation apparatus capable of exerting effects of, for example, reducing fatigue and improving the physical condition of a vehicle occupant.

Method of Solving the Problem

In order to solve the problem the vehicle thermal stimulation apparatus according to the first aspect is provided with: a biorhythm detector for detecting a biorhythm accompanying a periodic change in an occupant; a thermal stimulation generator that applies at least one thermal stimulus to the occupant; and a controller, operating the thermal stimulation generator with a phase difference to the biorhythm of an occupant detected by the biorhythm detector such that the thermal stimulus to the occupant by the thermal stimulation generator is synchronized with the biorhythm of the occupant.

In the vehicle thermal stimulation apparatus according to the first aspect, when a biorhythm accompanying a periodic change in the occupant is detected by the biorhythm detector, the thermal stimulation generator is operated by the controller on the basis of the detection result of the biorhythm detector, and thermal stimulus is applied to the occupant, in synchronization with the biorhythm of the occupant, by the operation of the thermal stimulation generator.

With respect to this, it is known that generally in people the autonomic nerve (sympathetic nerve and parasympathetic nerve) activity is enhanced when skin stimuli are applied to a person, for example when exhaling, and vital functions are enhanced (see, for example, 55$^{th}$ General Meeting/Educational Lecture of the Japanese Jiritsushinkei Gakkai [Autonomic Nerve Society], "Hari no seitai hannou to Jiritsushinkei (Dentouijutsu no kokoro wo kumi, kagakushiten ni tatsu shinkyuuryouhou)" [Bioresponse to Acupuncture and the Autonomic Nerve (Opening the Mind to Traditional Medicine, Acupuncture And Moxibustion from the Scientific Perspective)], Jiritsushinkei [Autonomic Nerve], Vol. 40, No. 1, page 26, published Feb. 15, 2003).

Accordingly, by applying thermal stimulus to the occupant so as to be synchronized with a biorhythm of the occupant, as in the vehicle thermal stimulation apparatus according to the first aspect, the vital functions can be enhanced by enhancing the autonomic nerve (parasympathetic nerve) activity of the occupant. It is thereby possible to exert effects of, for example, reducing fatigue and improving the physical condition of a vehicle occupant. However, in order for the thermal stimulation generator to apply thermal stimulus to the occupant so as to be synchronized with the biorhythm of the occupant, the thermal stimulation generator is operated with a phase difference to the biorhythm of the occupant using the controller. Therefore, for example, even though time is required from operation of the thermal stimulation generator to the actual application of thermal stimulus to the occupant, due to the influence on thermal transmission of materials present between the thermal stimulation generator and the occupant, by operating the thermal stimulation generator with a specific phase difference to the biorhythm of the occupant in the above described manner, thermal stimulus can still be applied to the occupant in synchronization with the biorhythm of the occupant. It is thereby possible to further enhance the exerted effects of, for example, reducing fatigue and improving the physical condition of a vehicle occupant.

In order to solve the problem, the vehicle thermal stimulation apparatus according to the second aspect is provided with: a biorhythm detector to detect a biorhythm of the occupant accompanying a periodic change in an occupant; a thermal stimulation generator that applies at least one thermal stimulus to the occupant and is configured to contact an occupant with a heat source and move the heat source away from the occupant; and a controller that operates the thermal stimulation generator on the basis of the detection result of the biorhythm detector such that the thermal stimulus to the occupant by the thermal stimulation generator is synchronized with the biorhythm of the occupant, moving the heat source into contact with, and away from, the occupant.

In the vehicle thermal stimulation apparatus according to a second aspect when the biorhythm accompanying a periodic change of an occupant is detected by the biorhythm detector, the thermal stimulation generator is operated on the basis of the detection result of the biorhythm detector by the controller, and thermal stimulus is applied to the occupant when the thermal stimulation generator contacts the heat source to the occupant, and thermal stimulation to the occupant ceases when the thermal stimulation generator contacts the heat source to the occupant. Thermal stimuli are applied to the occupant so as to be synchronized with the biorhythm of the occupant by such operation of the thermal stimulation generator. Accordingly, in a similar manner to as in the vehicle thermal stimulation apparatus of the first aspect, the vital functions can be enhanced by enhancing the autonomic nerve (parasympathetic nerve) activity of the occupant. It is thereby possible to exert effects of, for example, reducing fatigue and improving the physical condition of a vehicle occupant.

However, the vehicle thermal stimulation apparatus of the second aspect is configured with a heat source capable of being contacted to, or moved away from, the occupant, and so thermal stimulus can be applied to the occupant by maintaining the temperature of the heat source constant, and moving the heat source into contact with, or away from, the occupant. In so doing the necessity for temperature control of the heat source is removed, and a lowering of the cost thereof can be achieved.

The vehicle thermal stimulation apparatus according to the third aspect is the vehicle thermal stimulation apparatus according to the first aspect wherein the biorhythm detector detects a pulse rhythm of the occupant, and the controller operates the thermal stimulation generator on the basis of the detection result of the biorhythm detector such that the thermal stimulus to the occupant by the thermal stimulation generator is synchronized with the pulse rhythm of the occupant.

In the vehicle thermal stimulation apparatus according to the third aspect, when the pulse rhythm of the occupant is detected by the biorhythm detector, the thermal stimulation generator controller is operated on the basis of the detection result of the biorhythm detector such that the thermal stimulus to the occupant by the operation of the thermal stimulation generator is synchronized with the pulse rhythm of the occupant.

By so doing, the vehicle thermal stimulation apparatus according to the third aspect can apply thermal stimulus to an occupant so as to be synchronized with the respiration rhythm of the occupant, and the vital functions can be enhanced by enhancing the autonomic nerve (parasympathetic nerve) activity of the occupant. It is thereby possible to exert effects of, for example, reducing fatigue and improving the physical condition of a vehicle occupant.

The vehicle thermal stimulation apparatus according to the fourth aspect is the vehicle thermal stimulation apparatus according to the second aspect wherein the controller operates the thermal stimulation generator synchronized with the biorhythm of the occupant detected by the biorhythm detector.

In the vehicle thermal stimulation apparatus according to the fourth aspect when the biorhythm of the occupant is detected by the biorhythm detector, the controller operates the thermal stimulation generator synchronized with the biorhythm of the occupant detected by the biorhythm detector. It is thereby possible to apply thermal stimulus to the occupant in synchronization with the biorhythm of the occupant.

The vehicle thermal stimulation apparatus according to a sixth aspect is the vehicle thermal stimulation apparatus according to the any one of the first aspect, second aspect, or fourth aspect, wherein the thermal stimulation generator is configured so as to be capable of generating and absorbing heat.

In the vehicle thermal stimulation apparatus according to the sixth aspect, thermal stimulus is applied to the occupant when the thermal stimulation generator is operated so that heat is generated, and portions of the occupant which have had thermal stimulation applied thereto are cooled when the thermal stimulation generator is operated so that heat is absorbed.

Therefore, according to the vehicle thermal stimulation apparatus according to the sixth aspect, since thermal stimulation can be applied after portions of the occupant applied with thermal stimulation have been cooled, the change in temperature of the occupant before and after applying the thermal stimulation can be made greater. It is thereby possible to further enhance the exerted effects of, for example, reducing fatigue and improving the physical condition of a vehicle occupant.

The vehicle thermal stimulation apparatus according to a eighth aspect is the vehicle thermal stimulation apparatus according to the first aspect, second aspect, fourth aspect or sixth aspect, wherein the thermal stimulation generator is provided to a vehicle seat.

In the vehicle thermal stimulation apparatus according to the eighth aspect the thermal stimulation generator is provided to a vehicle seat. Therefore thermal stimulation may be applied to a vehicle occupant in a seated state in the vehicle seat.

The vehicle thermal stimulation apparatus according to a ninth aspect, is the vehicle thermal stimulation apparatus according to the second aspect, wherein the heat source is configured so as to be capable of switching between a heat generating state and a non-heat generating state, and the controller places the heat source in the heat generating state when the heat source is contacted to the occupant, and places the heat source in the non-heat generating state when the heat source is separated from the occupant.

According to the vehicle thermal stimulation apparatus of the ninth aspect, the heat source can be cooled by placing the heat source in the non-heat generating state when the heat source is separated from the occupant, and so the temperature change of the thermal stimulus to the occupant can be made greater. Thereby, further enhanced effects of, for example, reducing fatigue and improving the physical condition of a vehicle occupant, can be exerted.

The vehicle thermal stimulation apparatus according to a tenth aspect is the vehicle thermal stimulation apparatus according to the first aspect, wherein the biorhythm detector detects a respiration rhythm of the occupant, and the controller operates the thermal stimulation generator on the basis of the detection result of the biorhythm detector such that the thermal stimulus is applied to the occupant by the thermal stimulation generator in synchronization with the respiration rhythm of the occupant.

In the vehicle thermal stimulation apparatus according to the tenth aspect, when the respiration rhythm of the occupant is detected by the biorhythm detector, the thermal stimulation generator is operated by the controller on the basis of the detection result of the biorhythm detector, and by operation of the thermal stimulation generator the thermal stimulus is applied to the occupant in synchronization with the respiration rhythm of the occupant.

In this manner, according to the vehicle thermal stimulation apparatus of the tenth aspect, since thermal stimulus can be applied to the occupant in synchronization with the respiration rhythm of the occupant, the vital functions can be enhanced by enhancing the autonomic nerve (parasympathetic nerve) activity of the occupant. By so doing, it is possible to exert effects of, for example, reducing fatigue and improving the physical condition of a vehicle occupant.

Effect Of The Invention

As described above, according to the present invention it is possible to exert effects of, for example, reducing fatigue and improving the physical condition of a vehicle occupant.

BRIEF DESCRIPTION OF THE DRAWINGS

FIG. 15 is a block diagram showing the overall configuration of the modified example of the vehicle thermal stimulation apparatus according to the first to the third exemplary embodiments of the present invention;

FIG. 16 is a timing chart showing the operation of the modified example of the vehicle thermal stimulation apparatus according to the first to the third exemplary embodiments of the present invention;

BEST MODE OF IMPLEMENTING THE INVENTION

First Exemplary Embodiment

Explanation will now be given of a vehicle thermal stimulation apparatus 10 according to the first exemplary embodiment of the present invention.

Figure 1:
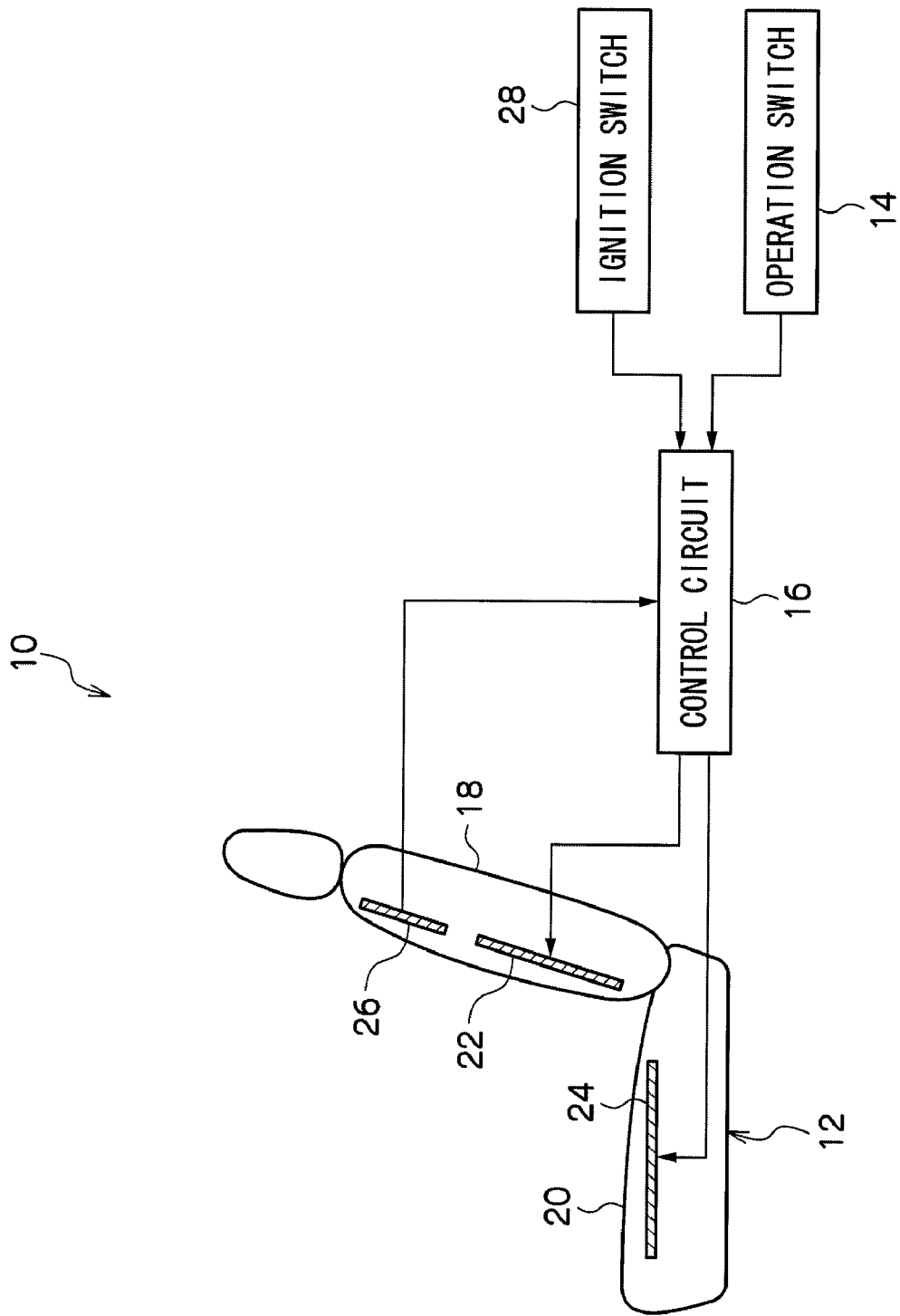
FIG. 1 is a block diagram showing the overall configuration of a vehicle thermal stimulation apparatus according to a first exemplary embodiment of the present invention.
Figure 2:
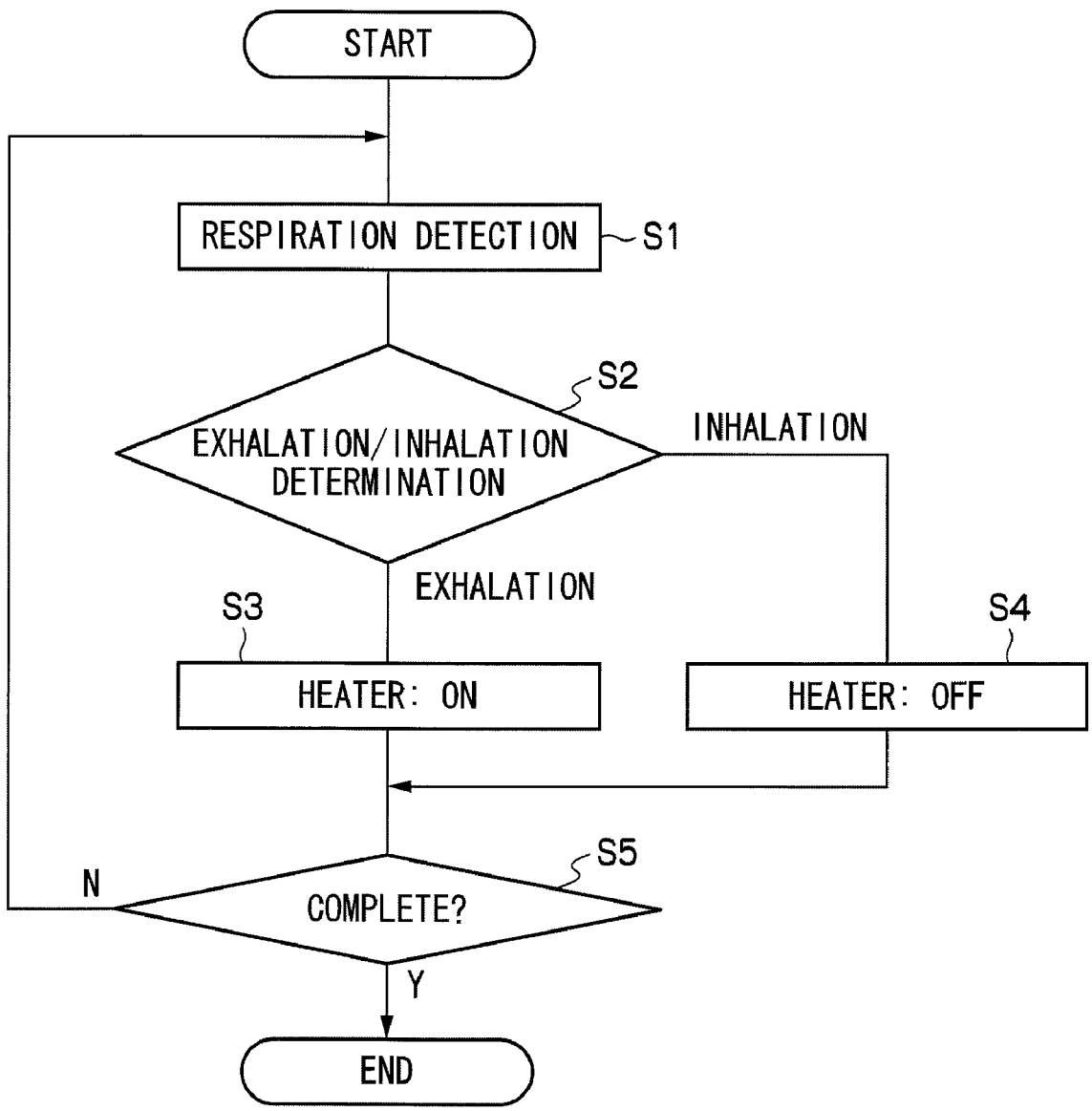
FIG. 2 is a flow chart showing the operation of the vehicle thermal stimulation apparatus according to the first exemplary embodiment of the present invention.
Figure 3:
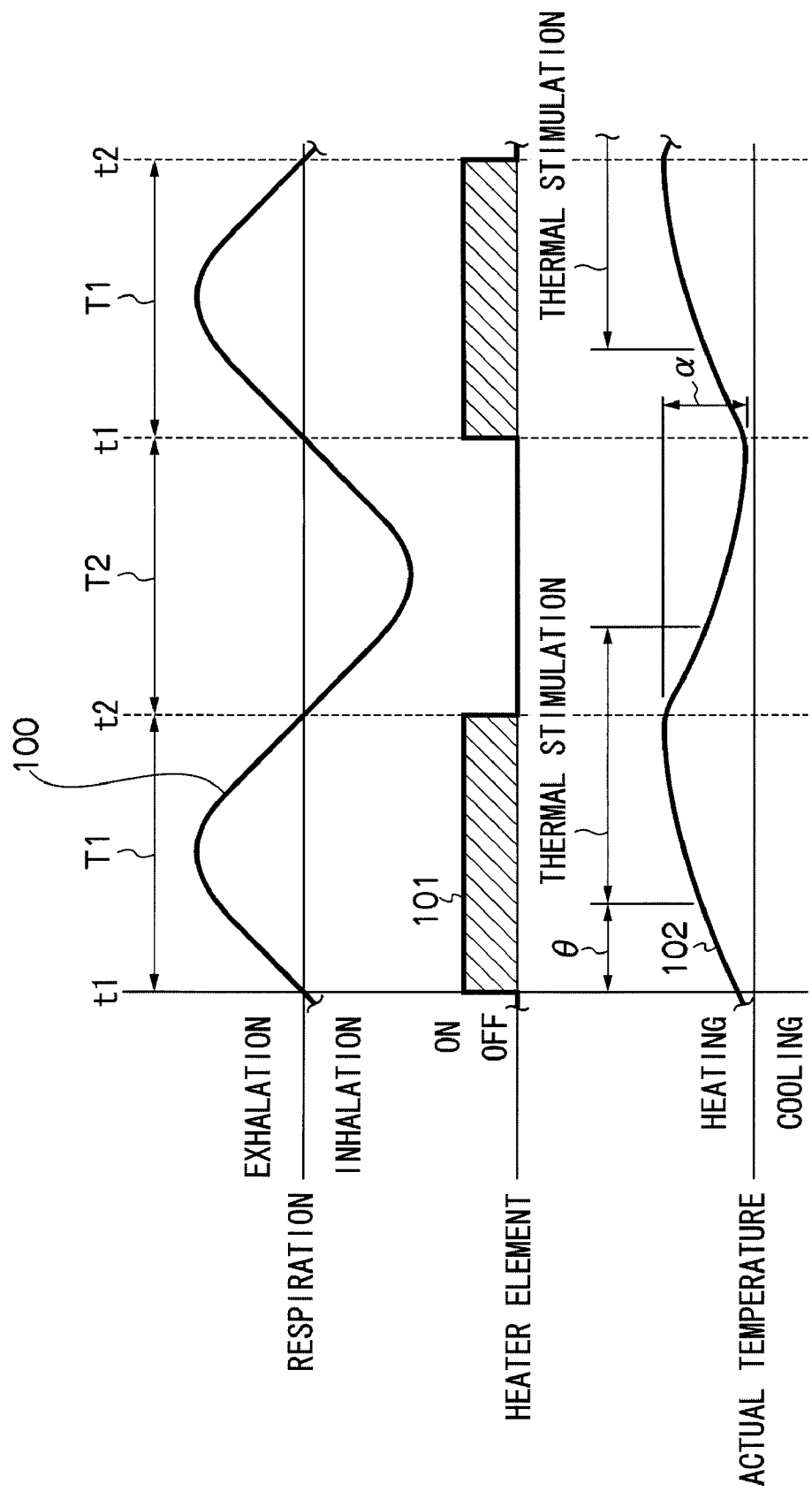
FIG. 3 is a timing chart showing the operation of the vehicle thermal stimulation apparatus according to the first exemplary embodiment of the present invention.
Figure 4:
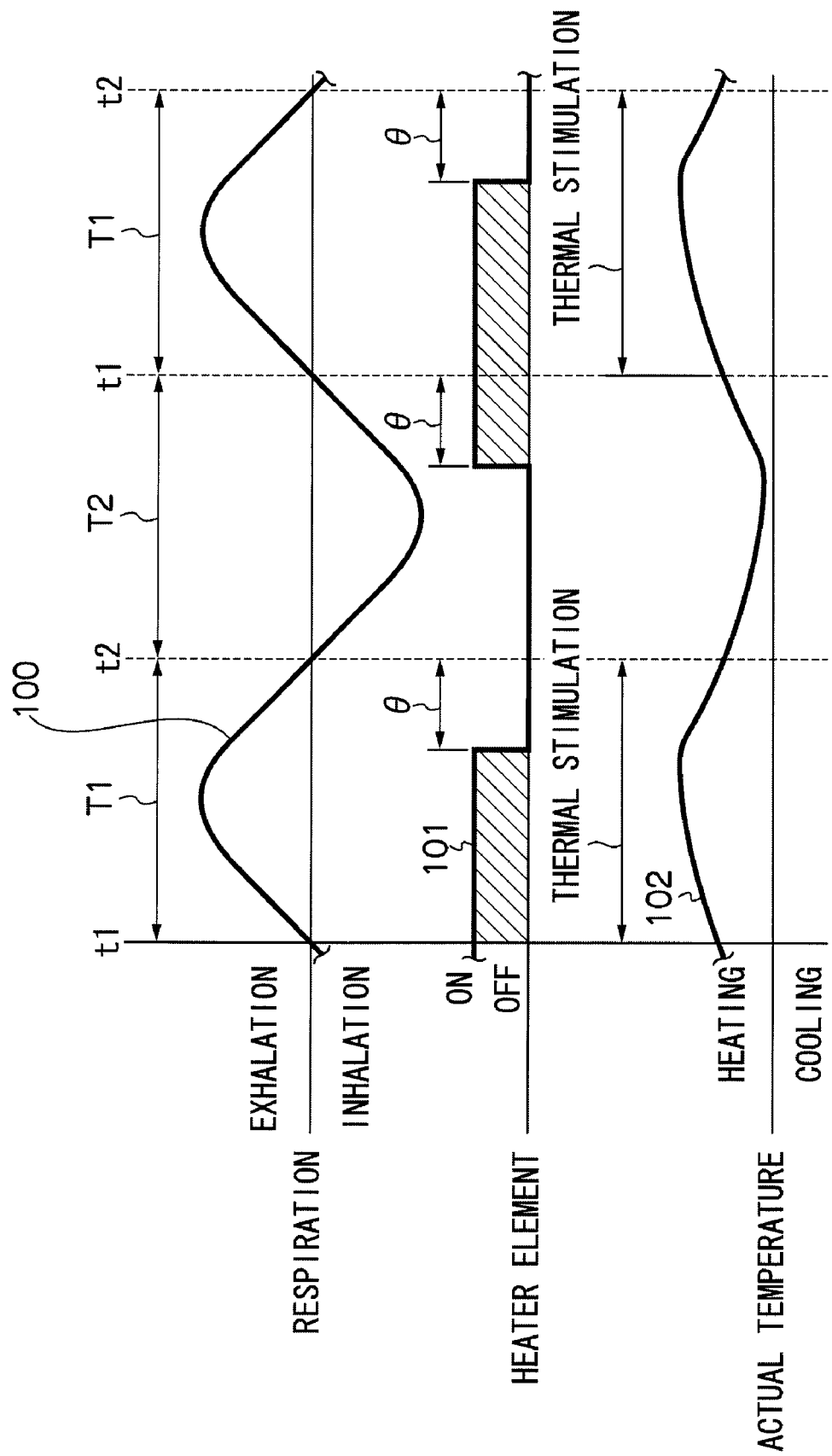
FIG. 4 is a timing chart showing the operation of a modified example of the vehicle thermal stimulation apparatus according to the first exemplary embodiment of the present invention.

FIG. 1 is a block diagram showing the overall configuration of the vehicle thermal stimulation apparatus 10 according to the first exemplary embodiment of the present invention. FIG. 2 is a flow chart showing the operation of the vehicle thermal stimulation apparatus 10 according to the first exemplary embodiment of the present invention. FIG. 3 is a timing chart showing the operation of the vehicle thermal stimulation apparatus 10 according to the first exemplary embodiment of the present invention.

The vehicle thermal stimulation apparatus 10 according to the first exemplary embodiment of the present invention is, for example, a device preferably applied to a vehicle such as an automobile. The vehicle thermal stimulation apparatus 10 is configured to include main components of a vehicle seat 12, an operation switch 14, and a control circuit 16, serving as a controller.

A seat back 18 and a seat cushion 20 are provided to the vehicle seat 12, and heater elements 22, 24, serving as thermal stimulation generators, are built into the seat front surface side of the seat back 18 and seat cushion 20, respectively. The heater elements 22, 24 are operated by the control circuit 16, configuration being made such that heat is generated when the heater elements 22, 24 are operated, warming each of the seat surfaces and applying thermal stimulus to an occupant seated thereon. It should be noted that in the present exemplary embodiment (and also in other exemplary embodiments) the thermal stimulation is, for example, stimulation such that when such thermal stimulation is applied an occupant is able to sense that thermal stimulation has been applied to the skin.

There is a piezoelectric sensor 26, serving as a biorhythm detector, built in above the heater element 22 at the seat front surface side of the seat back 18, the piezoelectric sensor 26 being capable of outputting a signal according to distortion thereof. The piezoelectric sensor 26 is disposed in a configuration so as to deform in accordance with the changes in shape of the upper body of a seated occupant which accompanying their respiration. Configuration is made, for example, such that the piezoelectric sensor 26 is able to output a positive signal on exhalation of the seated occupant and a negative signal inhalation of the seated occupant, as shown by the signal waveform 100 in FIG. 3.

The operation switch 14 is, for example, disposed to an instrument panel or the vehicle seat 12, and the operation switch 14 is configured so as to be capable of outputting a signal according to ON/OFF manipulation by the seated occupant.

The control circuit 16 is, for example, configured with an electrical circuit, including a CPU, ROM, RAM and the like, and the input portion of the control circuit 16 is connected to an ignition switch 28 and to the operation switch 14. The output portion of the control circuit 16 is connected to the heater elements 22, 24. Configuration is made such that the control circuit 16 operates the heater elements 22, 24 on the basis of the signals output from the piezoelectric sensor 26, the ignition switch 28 and the operation switch 14. Details regarding the operation of the control circuit 16 are described later.

Explanation will now be given of the operation of the vehicle thermal stimulation apparatus 10 according to the first exemplary embodiment of the present invention, as well as of the accompanying action and effect.

Program processing, as shown in the flow chart of FIG. 2, is initiated in the control circuit 16 when the switch-on signal output from the ignition switch 28, and the switch-on signal output from the operation switch 14 are input to the control circuit 16.

When the program processing as shown in the flow chart of FIG. 2 is initiated, first respiration of a seated occupant is detected by inputting the signal output from the piezoelectric sensor 26 to the control circuit 16 (step S1), and when this is undertaken determination is made as to whether the seated occupant's respiration is inhalation or exhalation, on the basis of the output signal from the piezoelectric sensor 26 (step S2).

With respect to the above, when the upper body of a seated occupant deforms accompanying respiration, the piezoelectric sensor 26 outputs a sign wave signal, as shown in signal waveform 100 of FIG. 3, the signal being positive during exhalation of the seated occupant and negative during the inhalation of the seated occupant.

When the control circuit 16 is input with a positive signal from the piezoelectric sensor 26, for example like the one shown in period T1 in the signal waveform 100 of FIG. 3, the control circuit 16 determines in the processing of the above step S1 that this signal relates to exhalation in the respiration of the seated occupant. The control circuit 16 outputs a signal like the one shown by signal waveform 101 in FIG. 3, and thereby switches on and operates the heater elements 22, 24 (step S3). When the heater elements 22, 24 are switched on and generating heat, the seat back 18 and the seat cushion 20 of the vehicle seat 12 are warmed, and the actual temperature of the surfaces thereof is raised, as shown by the temperature waveform 102 of FIG. 3. Thermal stimulation is thereby applied to the seated occupant.

When the control circuit 16 is input with a negative signal from the piezoelectric sensor 26, for example like the one shown in period T2 in the signal waveform 100 of FIG. 3, the control circuit 16 determines in the processing of the above step S1 that this signal relates to inhalation in the respiration of the seated occupant. The control circuit 16 outputs a signal like the one shown by signal waveform 101 in FIG. 3, and thereby switches off the heater elements 22, 24 (step S4). When the heater elements 22, 24 are switched off, the surfaces of the seat back 18 and the seat cushion 20 of the vehicle seat 12 are cooled by the air within the vehicle compartment, and the actual temperature of the surfaces thereof falls, like as shown by the temperature waveform 102 of FIG. 3.

Continuing, the control circuit 16 then determines, on the basis of the output signal from the ignition switch 28 and the output signal from the operation switch 14, whether or not one sequence of the program is complete (step S5), and when one routine of the program processing is not complete, the routine returns to the processing of step S1 described above. The processing of step S1 to step S4 is repeated until it is determined at S5 that the processing is complete. Thermal stimuli are thereby applied repeatedly to the seated occupant so as to be in synchronization with the respiration rhythm of the occupant, as shown in FIG. 3.

It is known that generally in people the autonomic nerve (sympathetic nerve and parasympathetic nerve) activity is enhanced when skin stimuli are applied to a person, for example, when exhaling and the vital functions are enhanced (see, for example, 55th General Meeting/Educational Lecture of the Japanese Jiritsushinkei Gakkai [Autonomic Nerve Society], "Hari no seitai hannou to Jiritsushinkei (Dentoujutsu no kokoro wo kumi, kagakushiten ni tatsu shinkyuuryouhou)" [Bioresponse to Acupuncture and the Autonomic Nerve (Opening the Mind to Traditional Medicine, Acupuncture And Moxibustion from the Scientific Perspective)], Jiritsushinkei [Autonomic Nerve], Vol. 40, No. 1, page 26, published Feb. 15, 2003).

Accordingly, by applying thermal stimulus to a seated occupant so as to be synchronized with the respiration rhythm of the seated occupant, as does the vehicle thermal stimulation apparatus 10 according to the present exemplary embodiment, the vital functions can be enhanced by enhancing the autonomic nerve (parasympathetic nerve) activity of the occupant. It is thereby possible to exert effects of, for example, reducing fatigue and improving the physical condition of a vehicle occupant.

Further, in the vehicle thermal stimulation apparatus 10 there are heater elements 22, 24 provided to the vehicle seat 12. Therefore, thermal stimulus can be applied to the vehicle occupant while in a seated state in the vehicle seat 12. In particular it is possible to exert effects of, for example, reducing fatigue and improving the physical condition of a driver by provision of the vehicle thermal stimulation apparatus 10 according to the present exemplary embodiment to the driver's seat.

Explanation will now be given of a modified example of the vehicle thermal stimulation apparatus 10 according to the first exemplary embodiment of the present invention.

In the above exemplary embodiment, the control circuit 16 is input with a output signal from the piezoelectric sensor 26 at a given timing in the processing of step S1, and determination of exhalation/inhalation of the seated occupant is made on the basis of the signal. Thermal stimuli are then repeatedly applied to the seated occupant in synchronization with the respiration rhythm of the occupant by switching the heater elements 22, 24 on and off according to the results of the determination, however, the following mode may also be adopted.

Namely, a signal output continuously output from the piezoelectric sensor 26 may be input to the control circuit 16, and the heater elements 22, 24 may be switched on in synchronization with when the respiration of the seated occupant changes over from inhalation to exhalation (i.e. at the timings t1 of FIG. 3), and the heater elements 22, 24 may be switched off in synchronization with when the respiration of the seated occupant changes over from exhalation to inhalation (i.e. at the timings t2 of FIG. 3). It is possible in this manner too to apply thermal stimulus to the occupant in synchronization with the respiration rhythm of the occupant, as shown in FIG. 3.

It should be noted that even if thermal stimulus is applied to the occupant so as to be in synchronization with the respiration rhythm of the occupant, like in the above exemplary embodiment and above modified example, in reality, for example, a delay (phase difference $\theta$) in the thermal stimulus to the occupant is sometimes generated due to the influence on the effectiveness of heat transfer of such materials as a cushion member or seat cover, present between the heater elements 22, 24 and the occupant. The following may therefore be adopted in such cases.

That is, the control circuit 16 may output a signal like that of the signal waveform 101 in response to the respiration rhythm of the occupant (i.e. to the signal waveform 100), such that the heater elements 22, 24 are off-set with a phase difference θ (advanced in phase) and there is no phase difference in thermal stimulus to the occupant of the heater elements 22, 24 relative to the respiration rhythm of the occupant.

By so doing, for example, even though time is required from operation of the heater elements 22, 24 to the actual application of thermal stimulus to the occupant, due to the influence on thermal transmission of such materials as a cushion member or seat cover present between the heater elements 22, 24 and the occupant, thermal stimulus can still be applied without a phase difference to the occupant in synchronization with the respiration rhythm of the occupant. It is thereby becomes possible to further enhance the exerted effects of, for example, reducing fatigue and improving the physical condition of a vehicle occupant.

Also, in the above exemplary embodiments, thermal stimulation is applied to the occupant by operating the heater elements 22, 24 each time the occupant exhales, however, for example, a mode may be adopted in which thermal stimulation is applied to the occupant by operating the heater elements 22, 24 at a ratio of one time of operation to plural times of exhalation.

Also, the heater elements 22, 24 in the above exemplary embodiments were built into the vehicle seat 12, however, the heater elements 22, 24 may be built into a door trim, an armrest, the steering wheel or the like. The thermal stimulation generator according to the present invention is also not limited to the heater elements 22, 24 and, for example, the thermal stimulation generator may be configured by an air conditioning unit, a halogen heater located near the feet, or the like.

The above exemplary embodiments also are configured such that detection is made of the respiration rhythm of the occupant using the piezoelectric sensor 26, however, configuration may be made such that an infrared sensor or other sensor detects the respiration rhythm of the occupant (i.e. by detecting the temperature of exhalation).

Second Exemplary Embodiment

Explanation will now be given of a vehicle thermal stimulation apparatus 50 according to the second exemplary embodiment of the present invention.

Figure 5:
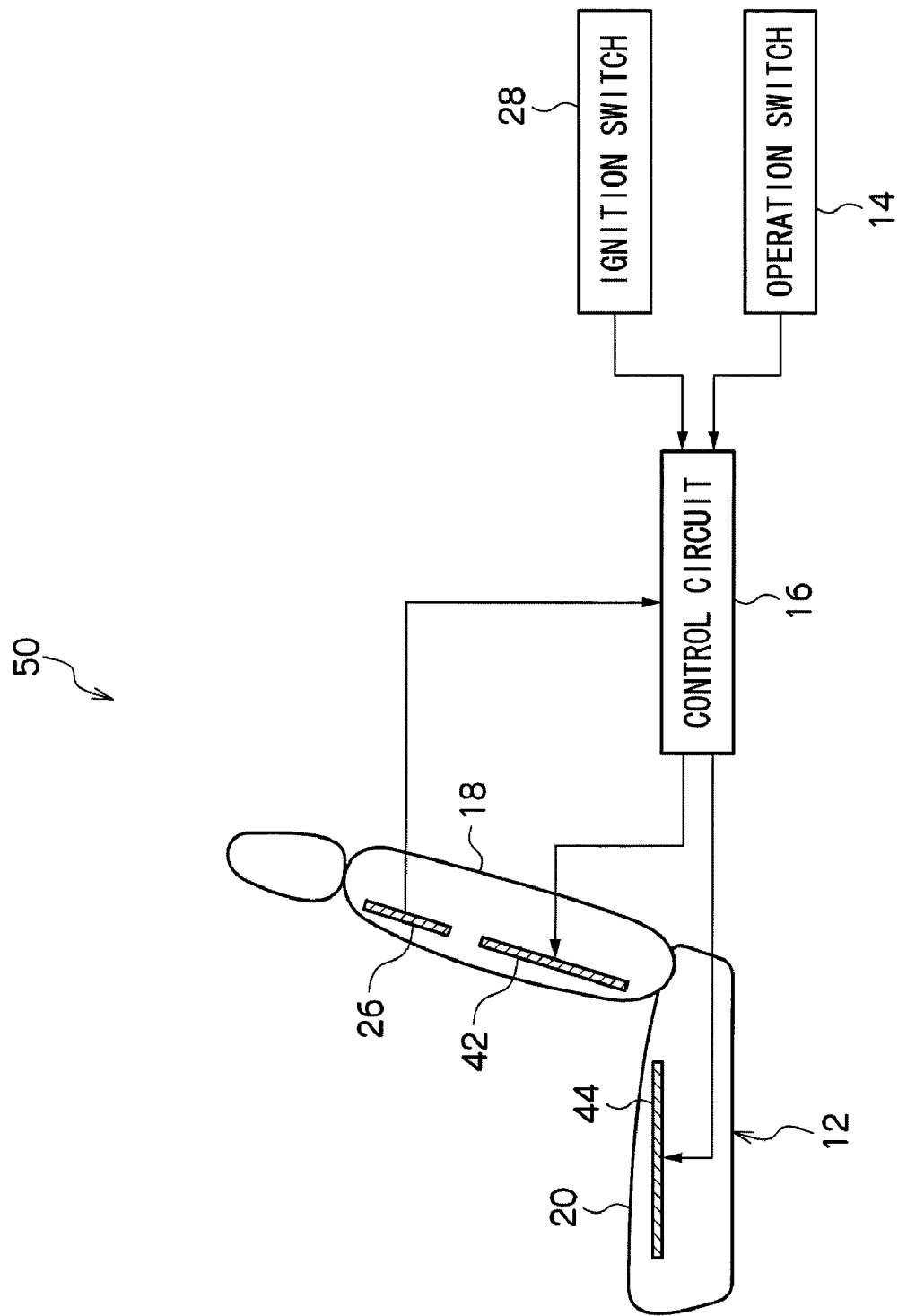
FIG. 5 is a block diagram showing the overall configuration of a vehicle thermal stimulation apparatus according to a second exemplary embodiment of the present invention.
Figure 6:
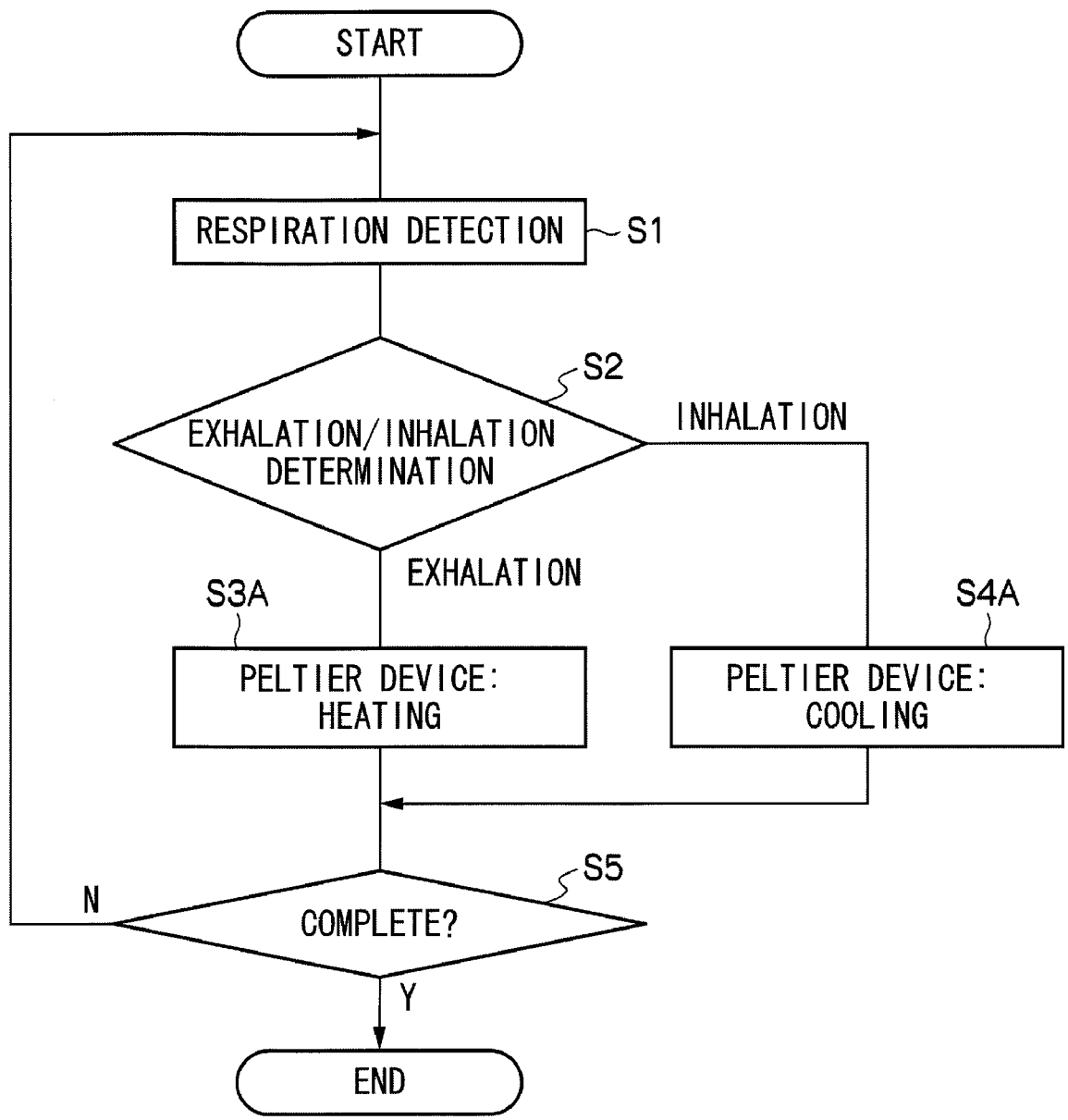
FIG. 6 is a flow chart showing the operation of the vehicle thermal stimulation apparatus according to the second exemplary embodiment of the present invention.
Figure 7:
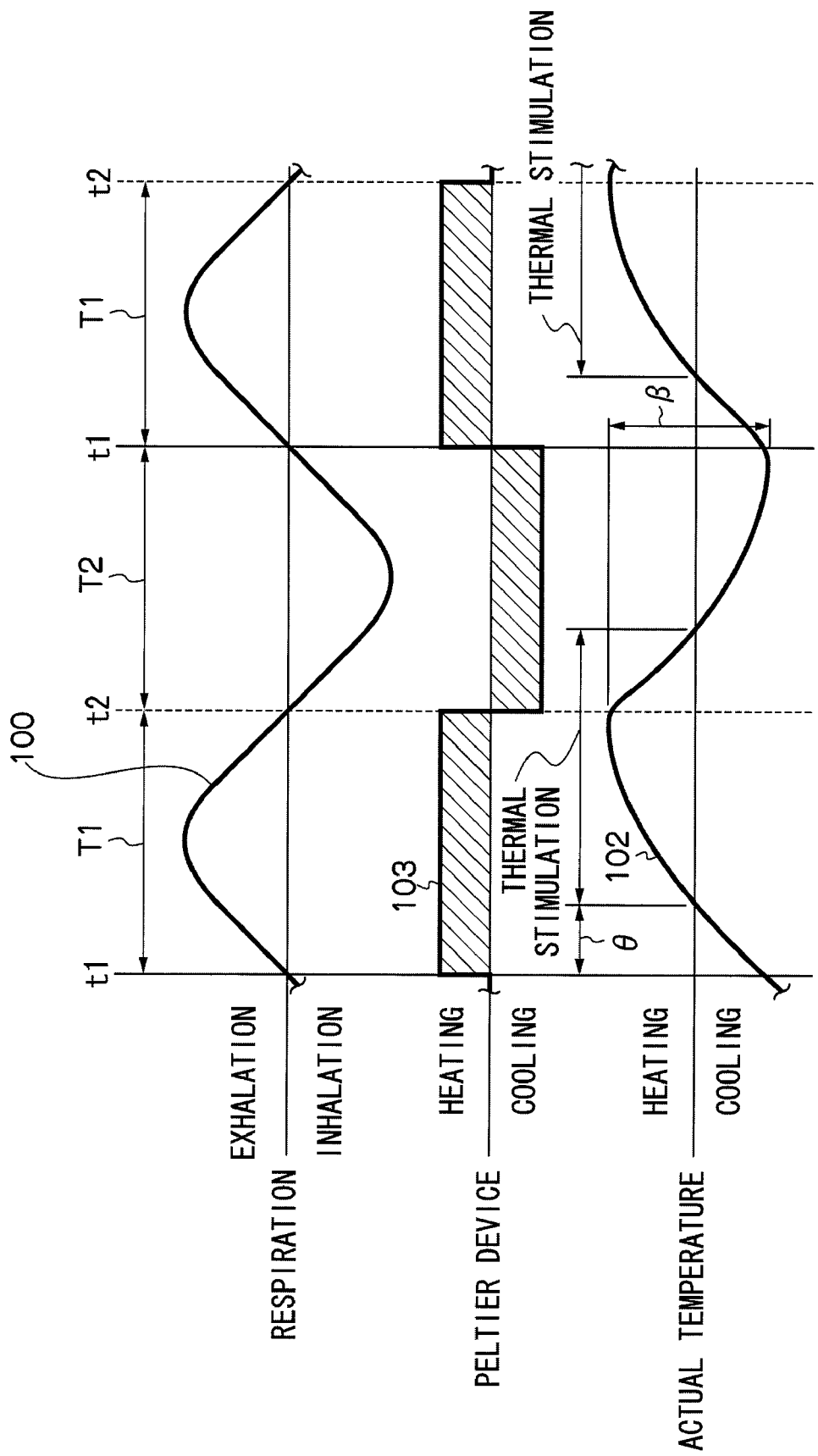
FIG. 7 is a timing chart showing the operation of the vehicle thermal stimulation apparatus according to the second exemplary embodiment of the present invention.

A block diagram is shown in FIG. 5 of the overall configuration of the vehicle thermal stimulation apparatus 50 according to the second exemplary embodiment of the present invention, a flow chart is shown in FIG. 6 of the operation of the vehicle thermal stimulation apparatus 50 according to the second exemplary embodiment of the present invention, and a timing chart is shown in FIG. 7 for the operation of the vehicle thermal stimulation apparatus 50 according to the second exemplary embodiment of the present invention.

The vehicle thermal stimulation apparatus 50 according to the second exemplary embodiment of the present invention shown in FIG. 5 is the vehicle thermal stimulation apparatus 10 according to the first exemplary embodiment of the present invention, with heating and cooling units 42, 44 provided as thermal stimulation generators in place of the heater elements 22, 24 of the vehicle thermal stimulation apparatus 10. Therefore the same reference numerals are applied to elements of the configuration of the vehicle thermal stimulation apparatus 50 according to the second exemplary embodiment of the present invention which are similar to those of the vehicle thermal stimulation apparatus 10 according to the first exemplary embodiment of the present invention, and explanation thereof will be omitted.

The heating and cooling units 42, 44 in the vehicle thermal stimulation apparatus 50 according to the second exemplary embodiment of the present invention are, for example, configured with plural Peltier devices (not shown). Each of these Peltier devices provided to the heating and cooling units 42, 44 are operated by the control circuit 16, and, for example, configuration is made such that heat is generated (heating operation) and heat is absorbed (cooling operation) according to the polarity of the voltage applied thereto from the control circuit 16. Each of the seat surfaces are warmed when heat is generated by the plural Peltier devices provided to the heating and cooling units 42, 44 and thermal stimulation is applied to the seated occupant, and each of the seat surfaces are cooled when heat is absorbed by the plural Peltier devices provided to the heating and cooling units 42, 44.

The output portion of the control circuit 16 is also connected to the heating and cooling units 42, 44, and the control circuit 16 controls the heating and cooling units 42, 44 according to the signals output from the piezoelectric sensor 26, the ignition switch 28, and the operation switch 14. Details regarding the operation of the control circuit 16 are given below.

Explanation will now be given of the operation of the vehicle thermal stimulation apparatus 50 according to the second exemplary embodiment of the present invention, and of the action and effect accompanying such operation.

The control circuit 16 of the vehicle thermal stimulation apparatus 50 according to the second exemplary embodiment of the present invention performs step S3A and step S4A shown in FIG. 6, in place of the program processing of step S3 and step S4 of the flow chart shown in FIG. 2 for the control circuit 16 in the vehicle thermal stimulation apparatus 10 according to the first exemplary embodiment of the present invention. Therefore explanation will be given of portions in the second exemplary embodiment of the present invention which differ from those of the first exemplary embodiment of the present exemplary embodiment, and reference should be made to the above explanation of the first exemplary embodiment for explanation of common portions thereto.

In the vehicle thermal stimulation apparatus 50 according to the second exemplary embodiment of the present invention, determination is made that the respiration of the seated occupant is exhalation when, during processing in step S1, the control circuit 16 is input with a positive signal from the piezoelectric sensor 26, like, for example, the one shown in periods T1 of the signal waveform 100 in FIG. 7, a signal is output like the one shown in periods T1 of the signal waveform 103 of FIG. 7, and each of the Peltier devices of the heating and cooling units 42, 44 is operated (step S3A) so as to generate heat (warming operation). When heat is generated by the heating and cooling units 42, 44, the seat back 18 and the seat cushion 20 of the vehicle seat 12 are warmed, and the actual temperature of the surfaces thereof is raised, like as shown in the temperature waveform 102 of FIG. 7. Thermal stimuli are thereby applied to the seated occupant.

In contrast, determination is made that the respiration of the seated occupant is inhalation when during processing in step S1 the control circuit 16 is input with a negative signal from the piezoelectric sensor 26, like, for example, the one shown in period T2 of the signal waveform 100 in FIG. 7, a signal is output like the one shown in period T2 of the signal waveform 103 of FIG. 7, and each of the Peltier devices of the heating and cooling units 42, 44 is operated (step S4A) so as to absorb heat (cooling operation). When heat is absorbed by the heating and cooling units 42, 44, the surfaces of the seat back 18 and the seat cushion 20 of the vehicle seat 12 are cooled, and the actual temperature of the surfaces is lowered, like as shown in the temperature waveform 102 of FIG. 7.

The control circuit 16 then performs the processing of the above described step S1 to step S4A repeatedly until processing is determined to be complete at step S5. Thermal stimuli are thereby applied repeatedly to the seated occupant in synchronization with the respiration rhythm of the occupant, as shown in FIG. 7.

Since it is possible to apply thermal stimulus to the seated occupant in synchronization with the respiration rhythm of seated occupant in this manner with the vehicle thermal stimulation apparatus 50 according to the present exemplary embodiment, the vital functions can be enhanced by enhancing the autonomic nerve (parasympathetic nerve) activity of the occupant. It is thereby possible to exert effects of, for example, reducing fatigue and improving the physical condition of a vehicle occupant.

Also, in the vehicle thermal stimulation apparatus 50 according to the present exemplary embodiment thermal stimulus is applied to the occupant when the heating and cooling units 42, 44 are operated so that heat is generated, and portions of the occupant which have had thermal stimulation applied thereto are cooled when the heating and cooling units 42, 44 are operated so that heat is absorbed. Therefore, according to the vehicle thermal stimulation apparatus 50 according to the present exemplary embodiment, since thermal stimulation can be applied after portions of the occupant that have been applied with thermal stimulation have been cooled, the change in temperature of the occupant before and after applying the thermal stimulation can be made greater.

Namely, there is a temperature change to the occupant of amplitude α (see FIG. 3) due to the ON/OFF operation of the heater elements 22, 24 such as in the vehicle thermal stimulation apparatus 10 of the first exemplary embodiment of the present invention. In contrast, when heat is generated and absorbed by the heating and cooling units 42, 44 of the vehicle thermal stimulation apparatus 50 according to the second exemplary embodiment of the present invention, a temperature change to the occupant of amplitude β, β being larger than α, is possible (see FIG. 7). It is thereby possible to further enhance the effect exerted of, for example, reducing fatigue and improving the physical condition of a vehicle occupant.

The heating and cooling units 42, 44 are also provided to the vehicle seat 12 in the vehicle thermal stimulation apparatus 50 according to the present exemplary embodiment. Therefore thermal stimulus can be applied to the vehicle occupant while in a seated state in the vehicle seat 12.

Explanation will now be given of a modified example of the vehicle thermal stimulation apparatus 50 according to the second exemplary embodiment of the present invention.

In the above exemplary embodiment, the control circuit 16 is input with a output signal from the piezoelectric sensor 26 at a given timing in the processing of step S1, and determination of exhalation/inhalation of the seated occupant is made on the basis of the signal, and thermal stimulus is then repeatedly applied to the seated occupant in synchronization with the respiration rhythm of the occupant by heating and cooling the heating and cooling units 42, 44 according to the results of the determination. However, the following mode may also be adopted.

Namely, a signal output continuously output from the piezoelectric sensor 26 may be input to the control circuit 16, and heating and cooling units 42, 44 may be heated in synchronization with when the respiration of the seated occupant changes over from inhalation to exhalation (i.e. at the timings t1 of FIG. 7), and the heating and cooling units 42, 44 may be cooled in synchronization with when the respiration of the seated occupant changes over from exhalation to inhalation (i.e. at the timings t2 of FIG. 7). It is possible in this manner too to apply thermal stimulus to the occupant in synchronization with the respiration rhythm of the occupant, as shown in FIG. 7.

Figure 8:
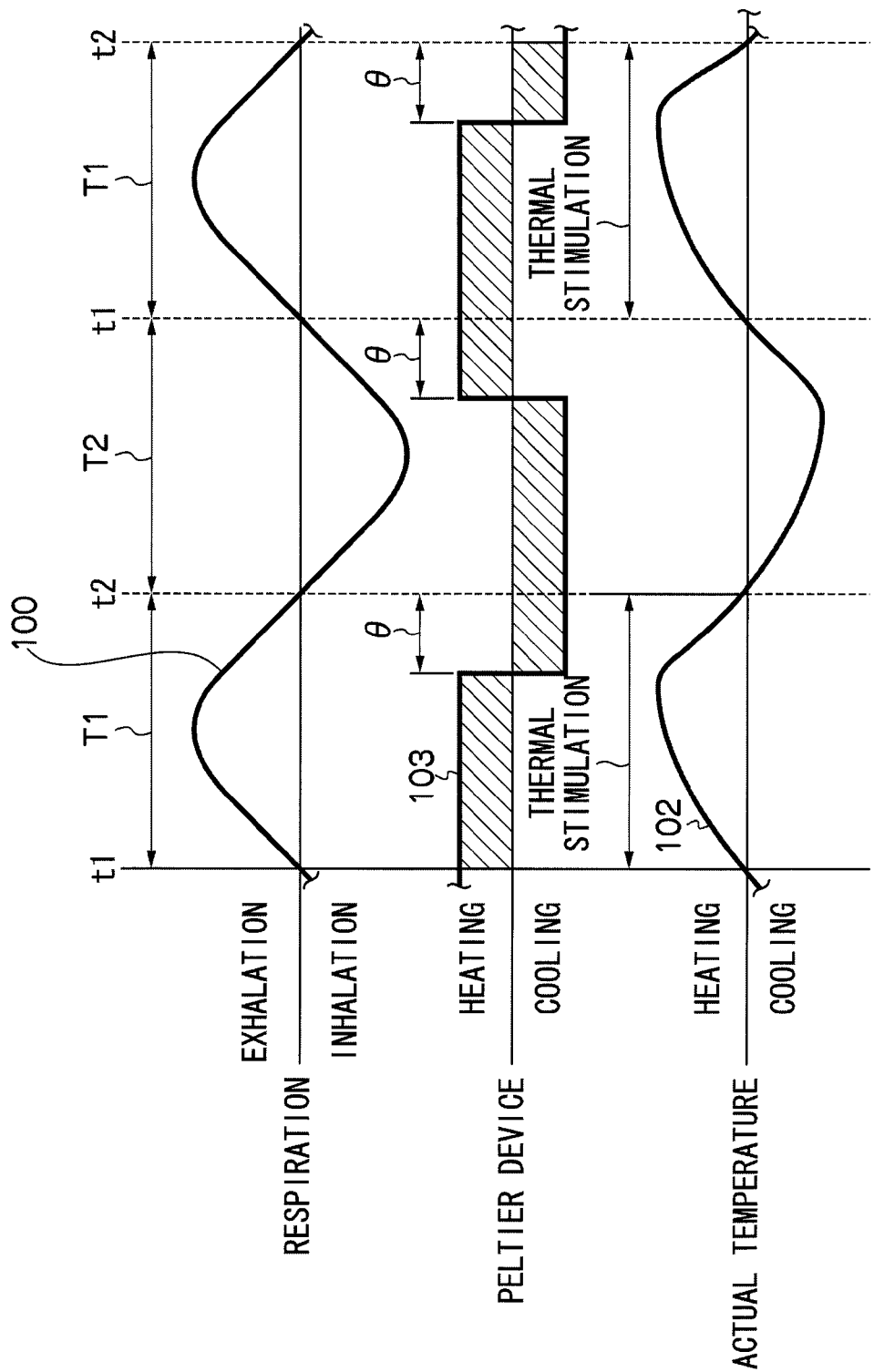
FIG. 8 is a timing chart showing the operation of a modified example of the vehicle thermal stimulation apparatus according to the second exemplary embodiment of the present invention.

Also, the control circuit 16 may output a signal like that of the signal waveform 103 in response to the respiration rhythm of the occupant (i.e. to the signal waveform 100), as shown in FIG. 8, such that the heating and cooling units 42, 44 are heated and cooled with a phase difference θ (advanced in phase) with respect to the respiration rhythm, but such that there is no phase difference in the actual temperature of the seat surfaces (thermal stimulation of the heating and cooling units 42, 44 to the occupant) relative to the respiration rhythm of the occupant.

By so doing, for example, even though time is required from operation of the heating and cooling units 42, 44 to the actual application of a change in temperature to the occupant, due to the influence on thermal transmission of such materials as a cushion member or seat cover present between the heating and cooling units 42, 44 and the occupant, thermal stimulus can still be applied without a phase difference to the occupant, in synchronization with the respiration rhythm of the occupant. It is thereby possible to further enhance the exerted effects of, for example, reducing fatigue and improving the physical condition of a vehicle occupant.

Also, in the above exemplary embodiments, thermal stimulus is applied to the occupant by heating the heating and cooling units 42, 44 each time the occupant exhales, however, for example, a mode may be adopted in which thermal stimulus is applied to the occupant by heating the heating and cooling units 42, 44 at a ratio of one time of heating to plural times of exhalation.

Also, the heating and cooling units 42, 44 in the above exemplary embodiments were built into the vehicle seat 12, however, the heating and cooling units 42, 44 may be built into a door trim, an armrest, the steering wheel or the like.

Obviously, for parts of the configuration of the vehicle thermal stimulation apparatus 50 according to the second exemplary embodiment of the present invention which are similar to parts of the above vehicle thermal stimulation apparatus 10 according to the first exemplary embodiment of the present invention, similar modifications may be made as are made in the modifications of the first exemplary embodiment.

Third Exemplary Embodiment

Explanation will now be given of a vehicle thermal stimulation apparatus 60 according to a third exemplary embodiment of the present invention.

Figure 9:
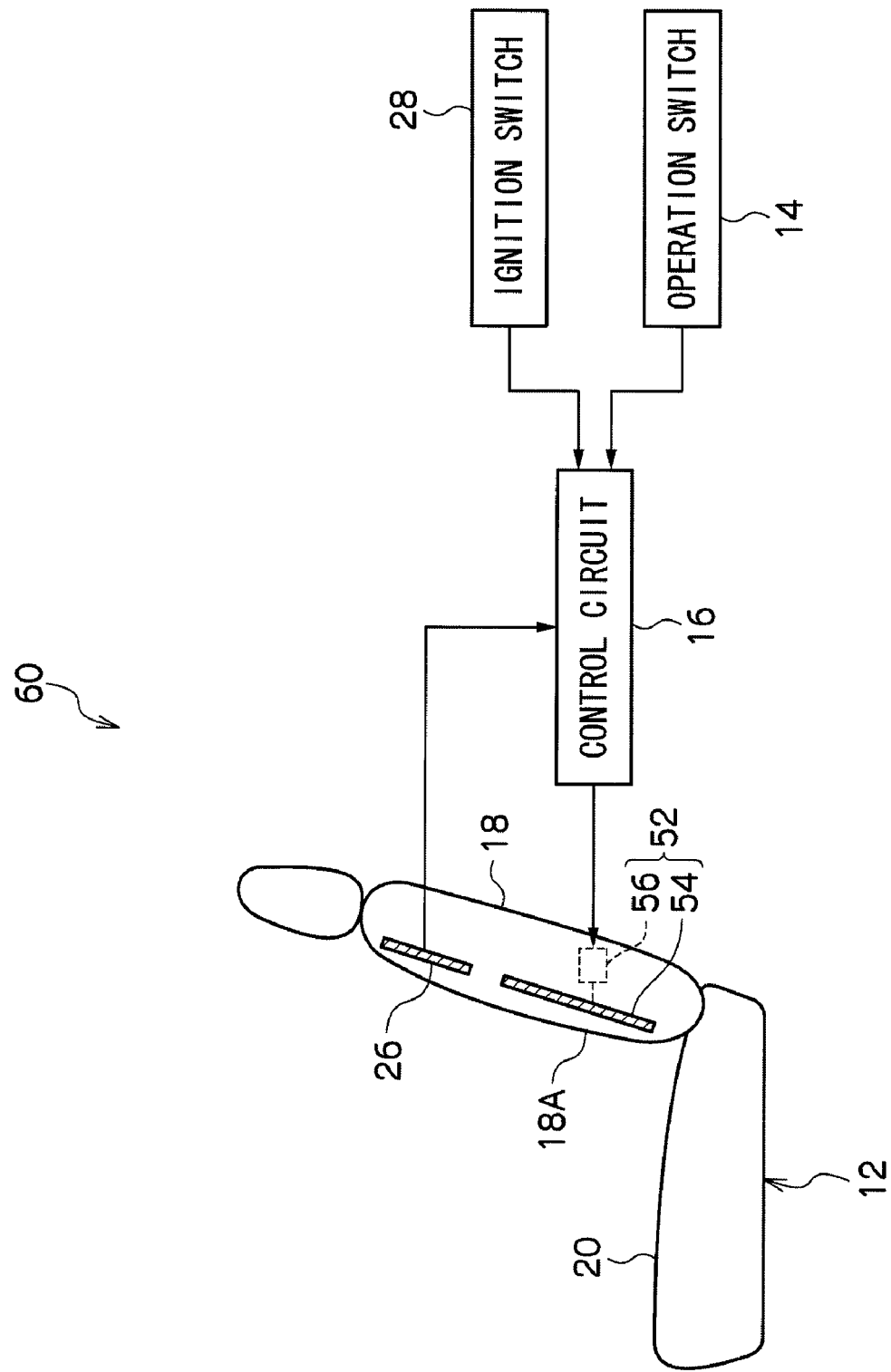
FIG. 9 is a block diagram showing the overall configuration of a vehicle thermal stimulation apparatus according to a third exemplary embodiment of the present invention.
Figure 10:
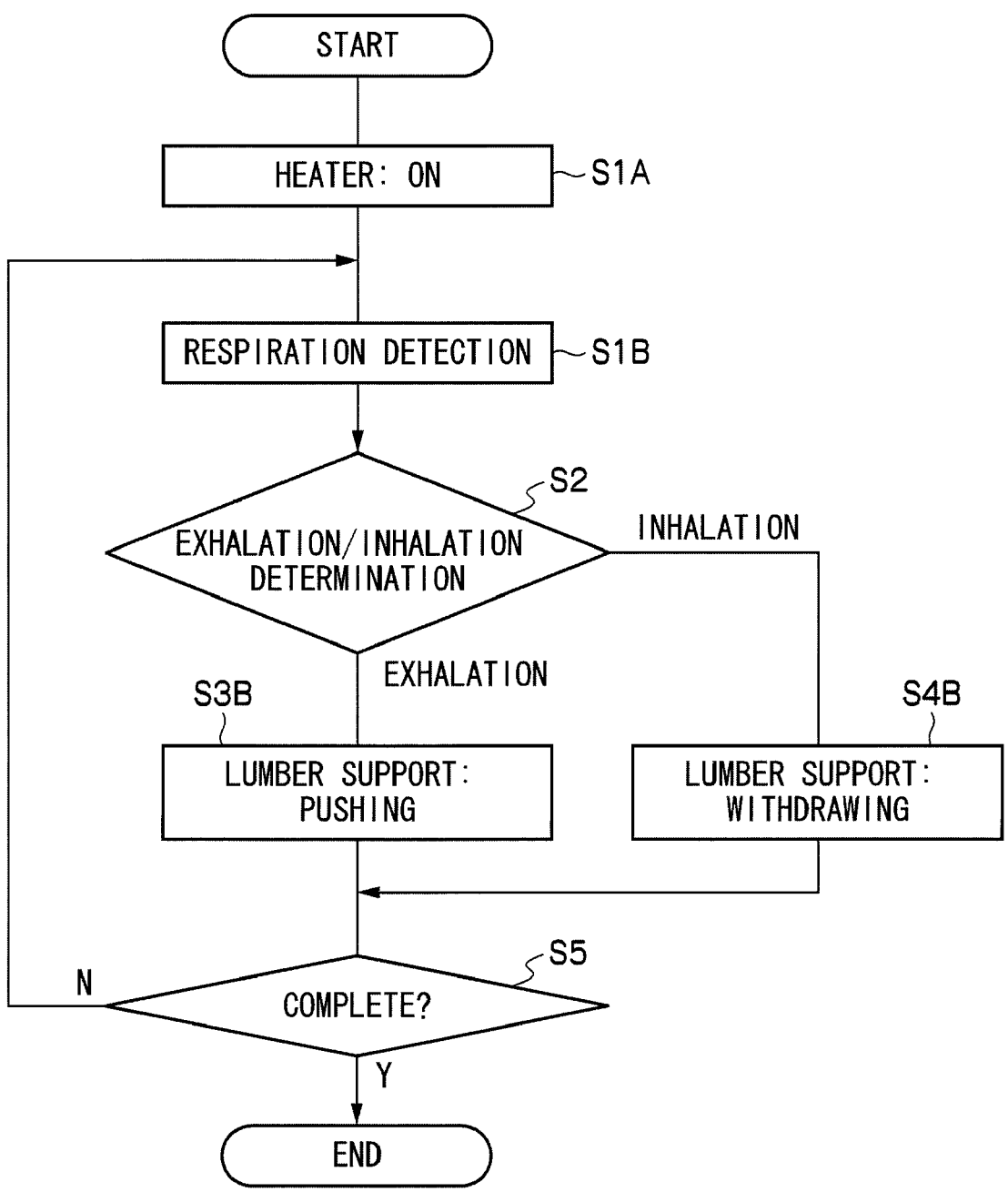
FIG. 10 is a flow chart showing the operation of the vehicle thermal stimulation apparatus according to the third exemplary embodiment of the present invention.
Figure 11A:
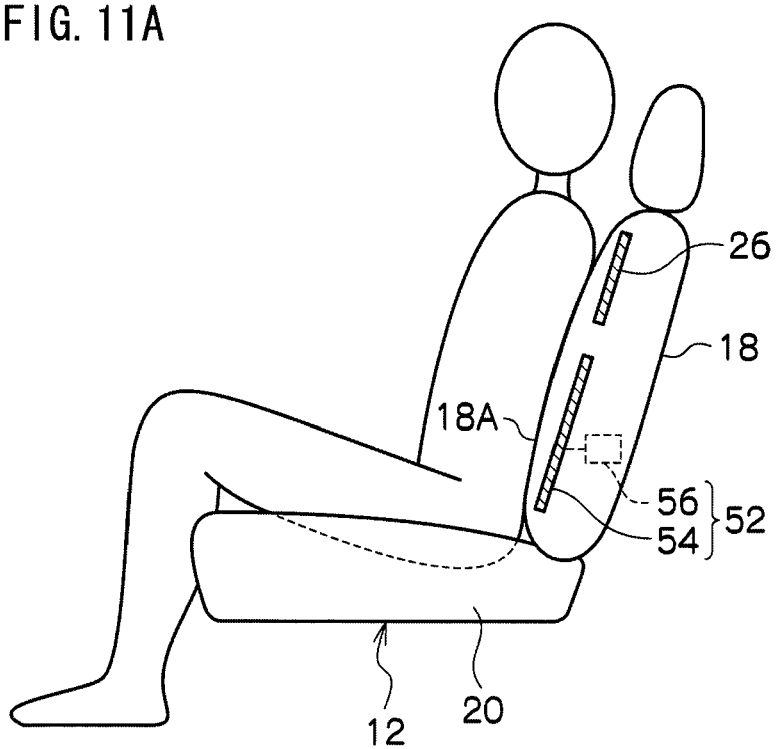
FIG. 11A is an explanatory diagram showing the operation of the vehicle thermal stimulation apparatus according to the third exemplary embodiment of the present invention.
Figure 11B:
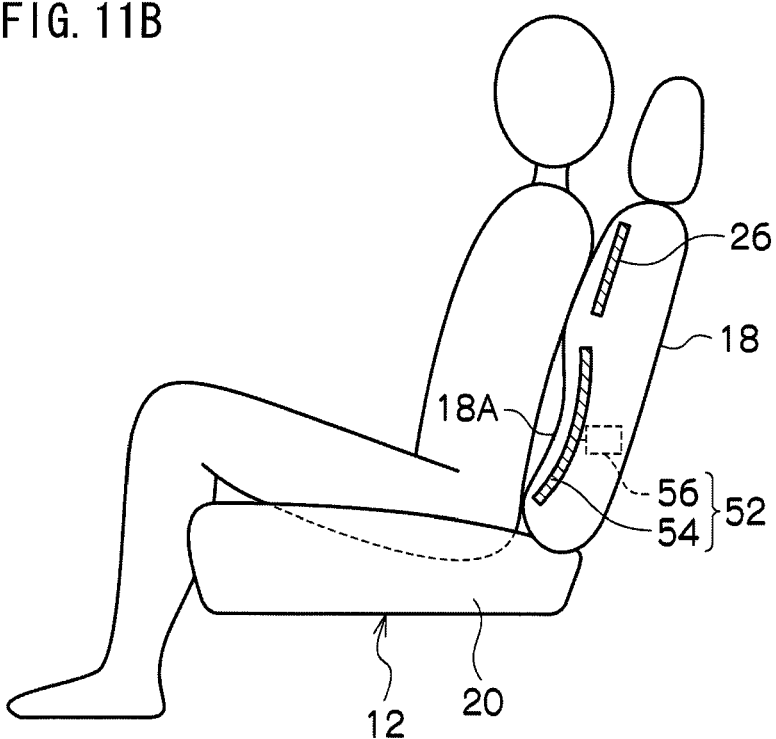
FIG. 11B is an explanatory diagram showing the operation of the vehicle thermal stimulation apparatus according to the third exemplary embodiment of the present invention.
Figure 12:
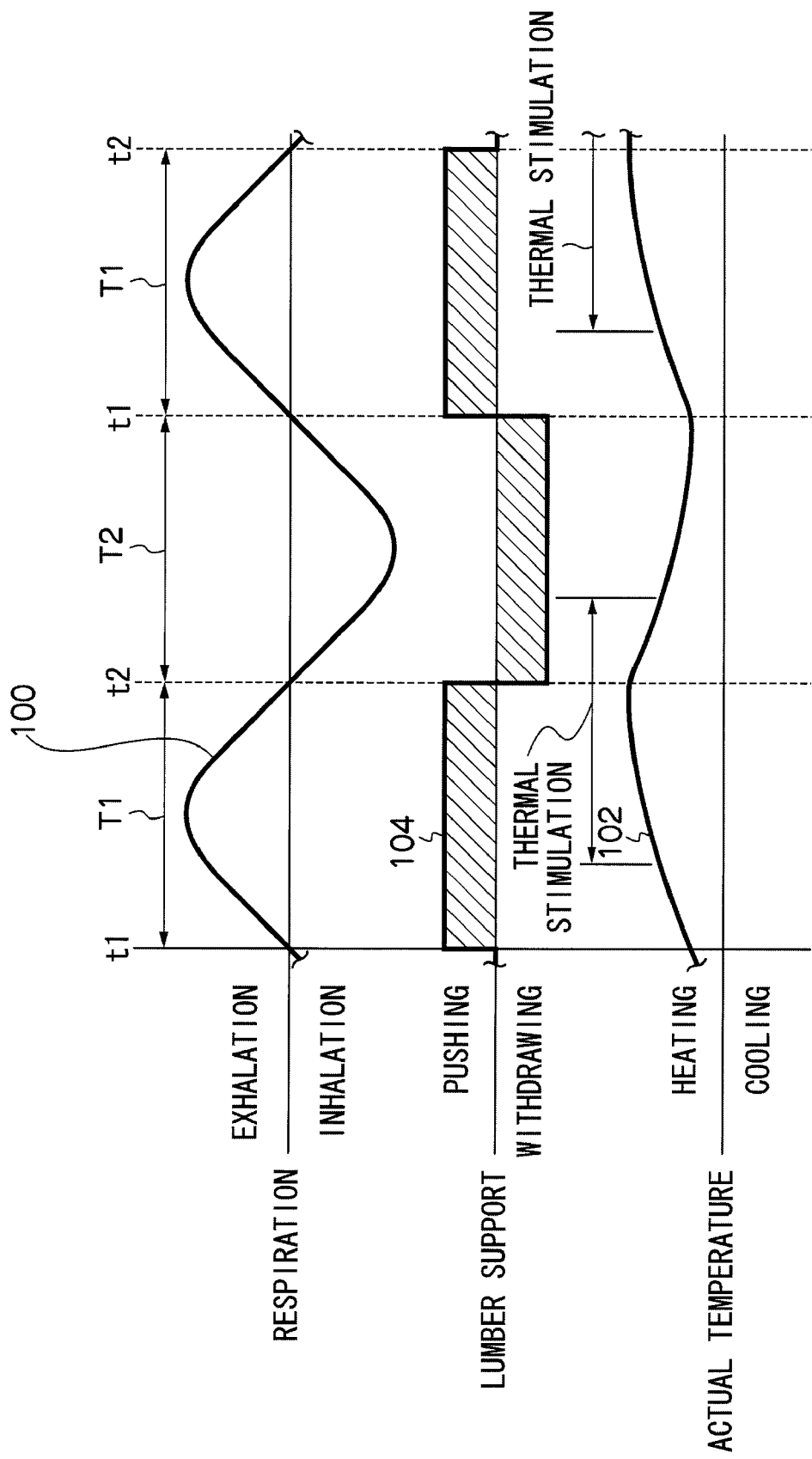
FIG. 12 is a timing chart showing the operation of the vehicle thermal stimulation apparatus according to the third exemplary embodiment of the present invention.

FIG. 9 is a block diagram showing the overall configuration of the vehicle thermal stimulation apparatus 60 according to the third exemplary embodiment of the present invention, FIG. 10 is a flow chart showing the operation of the vehicle thermal stimulation apparatus 60, FIG. 11A and FIG. 11B are explanatory diagrams showing the operation of the vehicle thermal stimulation apparatus 60 according to the third exemplary embodiment of the present invention, and FIG. 12 is a timing chart showing the operation of the vehicle thermal stimulation apparatus 60 according to the third exemplary embodiment of the present invention.

The vehicle thermal stimulation apparatus 60 according to the third exemplary embodiment of the present invention shown in FIG. 9 is the vehicle thermal stimulation apparatus 10 according to the first exemplary embodiment of the present invention in which a heater mounted movable lumber support 52 is provided as the thermal stimulation generator, in place of the heater elements 22, 24 of the vehicle thermal stimulation apparatus 10 according to the first exemplary embodiment of the present invention. Therefore in the vehicle thermal stimulation apparatus 60 according to the third exemplary embodiment of the present invention, portions thereof which are the same as those of the vehicle thermal stimulation apparatus 10 according to the first exemplary embodiment of the present invention are allocated the same reference numerals and explanation thereof is omitted.

The heater mounted movable lumber support 52 in the vehicle thermal stimulation apparatus 60 according to the third exemplary embodiment of the present invention is configured including a heater unit 54 and a drive unit 56. The heater unit 54 is driven by the control circuit 16 and configured so as to generate heat when operated, heating the seat front surface of a lumber support portion 18A of the seat back 18. The drive unit 56 is also controlled by the control circuit 16 and is configured so as to move, by pushing or withdrawing, the heater unit 54 in the direction of contact with, or separation from, the occupant.

Also, in the vehicle seat 12, configuration is made such that when the heater unit 54 is pushed by the drive unit 56 to the side approaching the occupant, the lumber support portion 18A of the seat back 18 also approaches (contacts) the occupant along with the heater unit 54, as shown in FIG. 11A, and when the heater unit 54 is withdrawn by the heater unit 54 to the side separated from the occupant, the lumber support portion 18A of the seat back 18 also separates from the occupant along with the heater unit 54.

In the present exemplary embodiment, thermal stimulus is applied to the seated occupant when the heater unit 54 of the heater mounted movable lumber support 52 approaches the occupant in a state of heat generation, and thermal stimulus to the seated occupant ceases when the heater unit 54 separates from the occupant.

The output portion of the control circuit 16 is also connected to the heater mounted movable lumber support 52, and the control circuit 16 is configured to control the heater mounted movable lumber support 52 on the basis of signals output from the piezoelectric sensor 26, the ignition switch 28 and the operation switch 14. Details of the operation of the control circuit 16 are given below.

Explanation will now be given of the operation of the vehicle thermal stimulation apparatus 60 according to the third exemplary embodiment of the present invention, and of the action and affects accompanying the operation thereof.

The control circuit 16 of the vehicle thermal stimulation apparatus 60 according to the third exemplary embodiment of the present invention performs step S1A, step S1B, step S3B and step S4B shown in FIG. 10, in place of the program processing of S1, step S3, and step S4 shown in the flow chart shown in FIG. 2 for the control circuit 16 in the vehicle thermal stimulation apparatus 10 according to the first exemplary embodiment of the present invention. Therefore explanation will be given below of portions in the third exemplary embodiment of the present invention which differ from those of the first exemplary embodiment of the present exemplary embodiment, and reference should be made to the above explanation of the first exemplary embodiment for explanation of common portions thereto.

When the control circuit 16 in the vehicle thermal stimulation apparatus 60 according to the third exemplary embodiment of the present invention initiates the program processing shown in the flow chart of FIG. 10, first the heater unit 54 of the heater mounted movable lumber support 52 is operated and caused to generate heat (step S1A). The seat surface of the lumber support portion 18A of the seat back 18 is thereby warmed.

Then the control circuit 16 detects the exhalation/inhalation of the seated occupant (step S1B) by being input with the output signal from the piezoelectric sensor 26, with this determination as to whether the respiration of the seated occupant is exhalation or inhalation being made on the basis of the output signal from the piezoelectric sensor 26 (step S2).

In the vehicle thermal stimulation apparatus 60 according to the third exemplary embodiment of the present invention, determination is made that the respiration of the seated occupant is exhalation when, during processing in step S1B, the control circuit 16 is input with a positive signal from the piezoelectric sensor 26, like, for example, the one shown in periods T1 of the signal waveform 100 in FIG. 12, a signal is output like the one shown in periods T1 of the signal waveform 104 of FIG. 12, and the drive unit 56 of the heater mounted movable lumber support 52 is operated in the direction of pushing (step S3B). Then, when the drive unit 56 is operated in the direction of pushing, the lumber support portion 18A of the seat back 18 also approaches the occupant together with the heater unit 54, as shown in FIG. 11A, and a thermal stimulus is applied to the seated occupant like that shown in temperature waveform 102 of FIG. 12.

In contrast, determination is made that the respiration of the seated occupant is inhalation when, during processing in step S1B, the control circuit 16 is input with a negative signal from the piezoelectric sensor 26, like, for example, the one shown in period T2 of the signal waveform 100 in FIG. 12, a signal is output like the one shown in period T2 of the signal waveform 104 of FIG. 12, and the drive unit 56 of the heater mounted movable lumber support 52 is moved in the withdrawing direction (step S4B). Then, when the drive unit 56 is operated in the withdrawing direction the lumber support portion 18A of the seat back 18 also separates from the occupant together with the heater unit 54, as shown in FIG. 11B, and the application of thermal stimulus to the seated occupant is thereby ceased, as shown in the temperature waveform 102 of FIG. 12.

The control circuit 16 repeatedly performs the processing of the above step S1A to step S4A until it is determined that processing is complete at step S5. Thermal stimuli are thereby applied to the seated occupant in synchronization with the respiration rhythm of the occupant, as shown in FIG. 12.

Since thermal stimulus can be applied in this manner to a seated occupant in synchronization with the respiration rhythm of the seated occupant with the vehicle thermal stimulation apparatus 60 according to the present exemplary embodiment, the vital functions can be enhanced by enhancing the autonomic nerve (parasympathetic nerve) activity of the occupant. It is therefore possible to exert effects of, for example, reducing fatigue and improving the physical condition of a vehicle occupant.

Also, in the vehicle thermal stimulation apparatus 60 according to the present exemplary embodiment, thermal stimulus can be applied to an occupant, even in a state as described above in which a uniform temperature is maintained of the heater unit 54, by moving the heater unit 54 in contact with and away from the occupant. By so doing there is no need for temperature control of the heater unit 54 and a lower cost can be achieved.

According to the vehicle thermal stimulation apparatus 60 of the present exemplary embodiment, in addition to the thermal stimulation, a physical stimulation can also be applied in synchronization with the respiration rhythm by pushing the lumber support portion 18A against the occupant, and a synergetic effect to the thermal stimulation can be obtained.

In the vehicle thermal stimulation apparatus 60 according to the present exemplary embodiment, thermal stimulus can also be applied to the vehicle occupant while in a seated state in the vehicle seat 12.

Explanation will now be given of a modified example of the vehicle thermal stimulation apparatus 60 according to the third exemplary embodiment of the present invention.

In the above exemplary embodiment the control circuit 16 is input with a output signal from the piezoelectric sensor 26 at a given timing in the processing step S1B, and determination of exhalation/inhalation of the seated occupant is made on the basis of the signal, thermal stimulus is then repeatedly applied to the seated occupant in synchronization with the respiration rhythm of the occupant by moving the heater unit 54 of the heater mounted movable lumber support 52 in contact with and away from the occupant according to the results of the determination. However, the following mode may also be adopted.

Namely, a signal output continuously output from the piezoelectric sensor 26 may be input to the control circuit 16, and the drive unit 56 of the heater mounted movable lumber support 52 may be operated in the direction of pushing in synchronization with when the respiration of the seated occupant changes over from inhalation to exhalation (i.e. at the timings t1 of FIG. 12), and the drive unit 56 of the heater mounted movable lumber support 52 may be operated in the withdrawing direction in synchronization with when the respiration of the seated occupant changes over from exhalation to inhalation (i.e. at the timings t2 of FIG. 12). It is possible in this manner too to apply thermal stimulus to the occupant in synchronization with the respiration rhythm of the occupant, as shown in FIG. 12.

Also, in the above exemplary embodiment, the heater unit 54 of the heater mounted movable lumber support 52 in the state of heat generation was moved in contact with and away from the occupant, however the following mode may also be adopted.

Namely, the heater unit 54 of the heater mounted movable lumber support 52 may be configured so as to be able to switch between a heat generating state and a non-heat generating state, with the heater unit 54 being in the heat generation state when contacting the occupant and the applying thermal stimulus to the occupant, and the heater unit 54 being in the non-heat generating state when the heater unit 54 is separated from the occupant. By so doing, since the heater unit 54 is in the non-heat generating state when separated from the occupant the heater unit 54 may be cooled, the change in temperature of the thermal stimulus to the occupant can be made greater. The effect exerted, of, for example, reducing fatigue and improving the physical condition of a vehicle occupant, may thereby be further enhanced.

Figure 13:
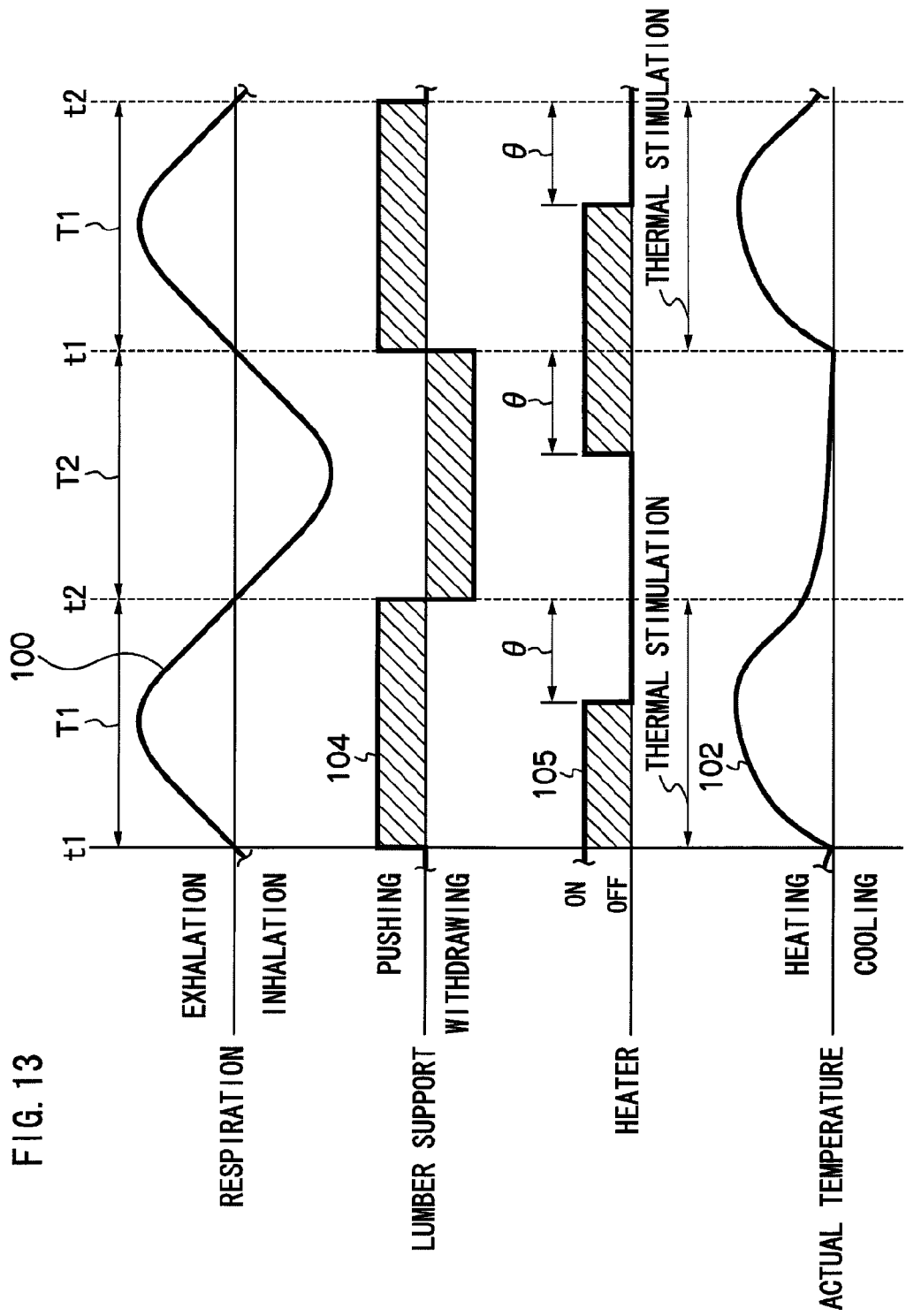
FIG. 13 is a timing chart showing the operation of a modified example of the vehicle thermal stimulation apparatus according to the third exemplary embodiment of the present invention.

Also, in such a case, the control circuit 16 may output a signal like that of the signal waveform 105 in response to the respiration rhythm of the occupant (i.e. to the signal waveform 100), as shown in FIG. 13, such that the heater unit 54 of the heater mounted movable lumber support 52 is ON/OFF operated with a phase difference θ (advanced in phase) to the respiration rhythm, but such that there is no phase difference in the actual temperature of the seat surfaces (thermal stimulation of the heating and cooling units 42, 44 to the occupant) relative to the respiration rhythm of the occupant.

By so doing, for example, even though time is required from operation of the heater unit 54 and arriving at the heat generating state to the actual application of a change in temperature to the occupant, due to the influence on thermal transmission of such materials as a cushion member or seat cover present between the heater unit 54 and the occupant, thermal stimulus can still be applied without a phase difference to the occupant in synchronization with the respiration rhythm of the occupant. It is thereby possible to further enhance the exerted effects of, for example, reducing fatigue and improving the physical condition of a vehicle occupant.

Also, in the above exemplary embodiment, thermal stimulus is applied to the occupant by operating the drive unit 56 of the heater mounted movable lumber support 52 in the direction of pushing each time the occupant exhales, however, for example, a mode may be adopted in which thermal stimulus is applied to the occupant by operating the drive unit 56 of the heater mounted movable lumber support 52 in the direction of pushing at a ratio of one time of operation to plural times of exhalation.

Also, in the above exemplary embodiments the heater unit 54 is built into the lumber support portion 18A of the vehicle seat 12, and thermal stimulus is applied to the occupant by moving the heater unit 54 in contact with and away from the occupant. However, the heater unit 54 may be built into a thigh support portion (a support portion at the back face of the thighs) or the like, and thermal stimulation applied to the occupant by moving the heater unit 54 in contact with and away from the occupant. The heater unit 54 may be built into other components than the vehicle seat 12, such as into a door trim, an arm rest, a steering wheel or the like, and thermal stimulation applied to the occupant by moving such a heater unit 54 in contact with and away from the occupant.

Obviously, for parts of the configuration of the vehicle thermal stimulation apparatus 60 according to the third exemplary embodiment of the present invention which are similar to parts of the above vehicle thermal stimulation apparatus 10 according to the first exemplary embodiment of the present invention, similar modifications may be made as are made in the modifications of the first exemplary embodiment.

Common Modified Examples to each of the Exemplary Embodiments

Explanation is given below of common modified examples to each of the above exemplary embodiments.

Modified Example 1

Thermal stimuli are applied to the occupant in synchronization with a respiration rhythm in the above vehicle thermal stimulation apparatuses 10, 50, 60 according to the first to the third exemplary embodiments of the present invention, with the change over from exhalation to inhalation of the occupant used as the respiration rhythm. However, thermal stimulation may be applied to the occupant in synchronization with a respiration rhythm by using shifts of changes in the respiration rate of the occupant as the respiration rhythm.

Figure 14:
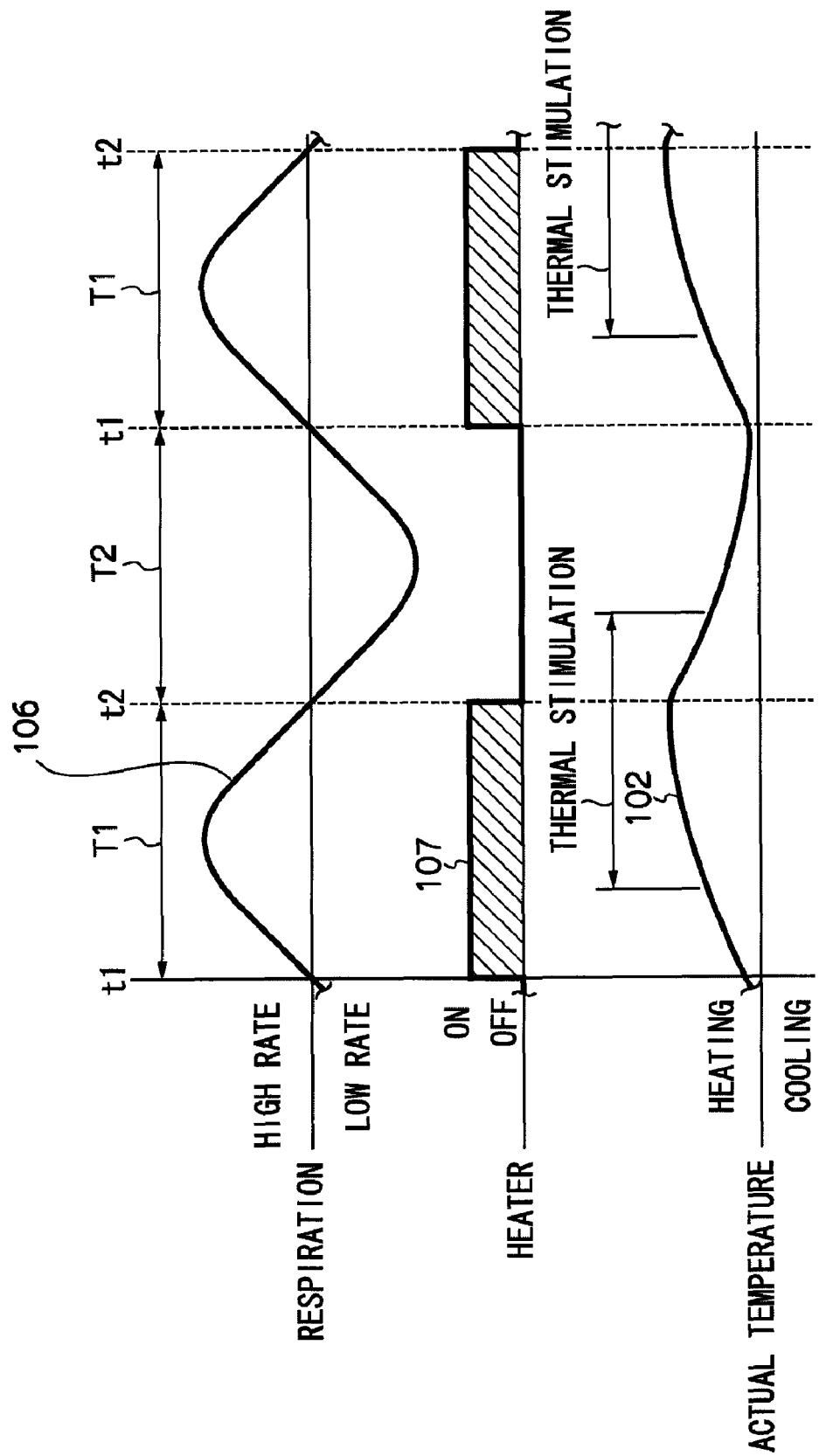
FIG. 14 is a timing chart showing the operation of a modified example of the vehicle thermal stimulation apparatus according to the first to the third exemplary embodiments of the present invention.

Namely, when the respiration rate is high, like in the periods T1 of the respiration rhythm waveform 106 of FIG. 14, the heaters are switched on by outputting a signal like the one in the periods T1 of the signal waveform 107, and thermal stimulus is applied to the occupant. When the respiration rate is low, like in the period T2 of the respiration rhythm waveform 106 of FIG. 14, the heaters are switched off by outputting a signal like the one in the period T2 of the signal waveform 107, to give a state in which thermal stimulus to the occupant is ceased.

Also, in such cases, for example, the respiration rhythm of the shifts in changes in the respiration rate of the occupant may be estimated from fluctuations in the output of an electrocardiographic sensor buried in the steering wheel.

Modified Example 2

In the vehicle thermal stimulation apparatuses 10, 50, 60 according to the first to the third exemplary embodiments of the present invention, configuration is made such that, the respiration rhythm of the occupant is detected as an example of a biorhythm of the occupant, and thermal stimulus is applied to the occupant in synchronization with the respiration rhythm. However, configuration may be made such that another biorhythm is detected, and thermal stimulus is applied to the occupant in synchronization with this biorhythm.

For example, an electrocardiometer 66 may be provided as a biorhythm detector capable of detecting the electrocardiographic waveform of the occupant, as in the vehicle thermal stimulation apparatus 70 shown in FIG. 15, and configuration may be made such that the control circuit 16 operates the heater elements 22, 24 on the basis of the detected signal from the electrocardiometer 66 such that the actual temperature peak of the seat surface, like that shown in temperature waveform 102 of FIG. 16, matches the R wave (waveform peak) of the electrocardiographic waveform 108 detected from the occupant, like the one shown in FIG. 16.

Thermal stimuli can also be applied to a seated occupant in synchronization with the pulse rhythm of the seated occupant in this manner, and the vital functions can be enhanced by enhancing the autonomic nerve (parasympathetic nerve) activity of the occupant. It is possible thereby to exert effects of, for example, reducing fatigue and improving the physical condition of a vehicle occupant.

It should be noted that, whereas in the present modified example thermal stimulus is applied to the occupant by operating the heater elements 22, 24 for each R wave detected in the electrocardiographic waveform from the occupant, the thermal stimulation may be applied to the occupant by operating the heater elements 22, 24 at the ratio of one time of operation to plural times that an R wave of the electrocardiographic waveform is detected from the occupant.

Modified Example 3

In the above Modified Example 2, R waves are detected in the electrocardiographic waveform from the occupant and thermal stimulus is applied to the occupant for each R wave, however, thermal stimulation may be applied to the occupant in synchronization with a pulse rhythm, using shifts in the pulse rate of the occupant as the pulse rhythm.

Figure 17A:
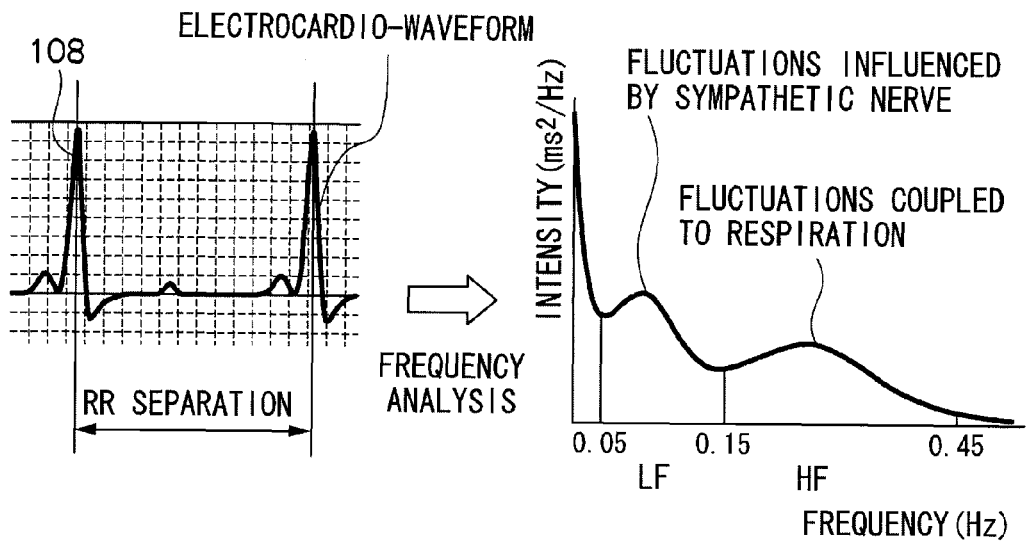
FIG. 17A is an explanatory diagram showing the modified example of the vehicle thermal stimulation apparatus according to the first to the third exemplary embodiments of the present invention.

Namely, as shown in FIG. 17A, continuous detection of the electrocardiographic waveform 108 of the occupant can be made and the intervals between R waves frequency analyzed in the electrocardiographic waveform 108. When this is undertaken, for example, fluctuations occur such as fluctuations in the interval (frequency) of the R waves in the electrocardiographic waveform due to the influence of the sympathetic nerves, fluctuations coupled to respiration, and the like.

Figure 17B:
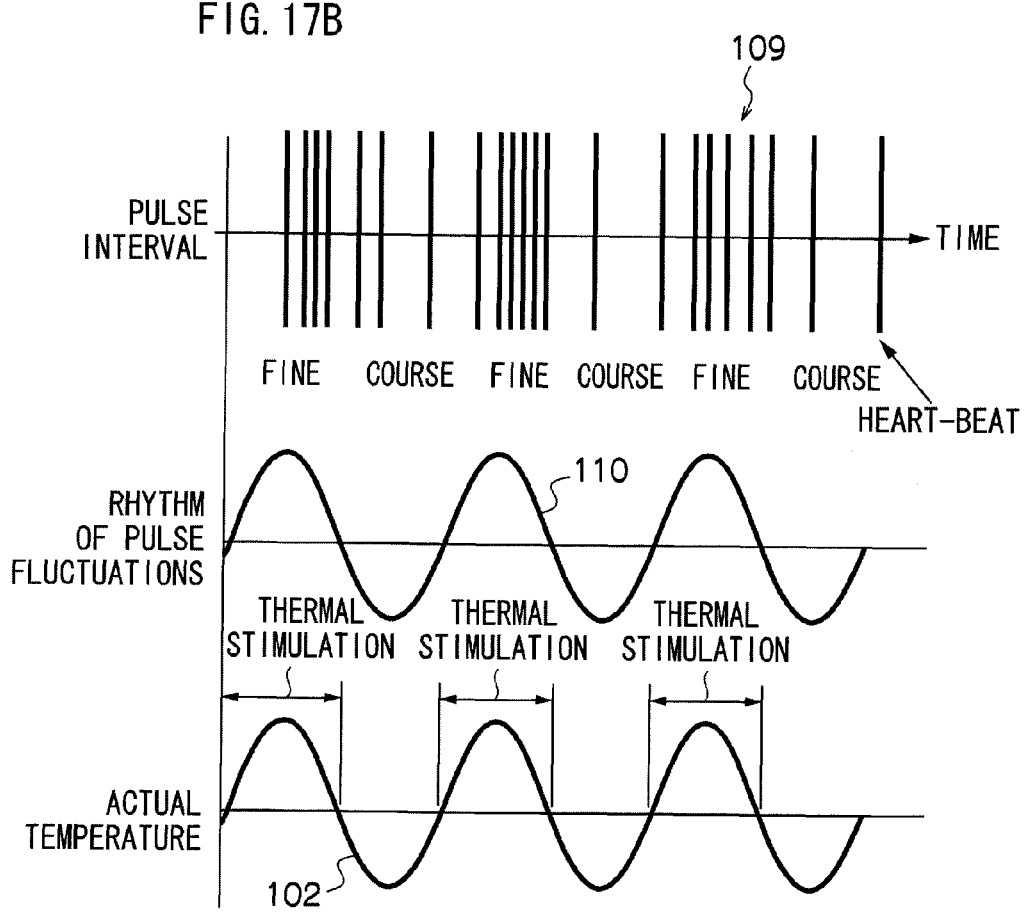
FIG. 17B is an explanatory diagram showing the modified example of the vehicle thermal stimulation apparatus according to the first to the third exemplary embodiments of the present invention.

Then, for example, as shown in FIG. 17B, a rhythm 110 is obtained of fluctuations in pulse from shifts in the pulse rate of the occupant according to the course-fine intervals 109 between the R waves of the electrocardiographic waveform detected from the occupant, and thermal stimulation may be applied to the occupant in synchronization with the rhythm 110 of pulse fluctuations.

Thermal stimuli can be applied to a seated occupant in synchronization with the pulse rhythm of the seated occupant in this manner too, and the vital functions can be enhanced by enhancing the autonomic nerve (parasympathetic nerve) activity of the occupant. It is possible thereby to exert effects of, for example, reducing fatigue and improving the physical condition of a vehicle occupant.

INDUSTRIAL APPLICABILITY

With the present invention it is possible to exert effects of, for example, reducing fatigue and improving the physical condition of a vehicle occupant by applying thermal stimulus to a vehicle occupant, and the present invention can preferably be mounted to a vehicle such as an automobile.

EXPLANATION OF THE REFERENCE NUMERALS

10, 50, 60, 70 vehicle thermal stimulation apparatus
12 vehicle seat
16 control circuit
22, 24 heater elements (thermal stimulation generators)
26 piezoelectric sensor (biorhythm detector)
42, 44 heating and cooling units (thermal stimulation generators)
52 movable lumber support (thermal stimulation generator)
66 electrocardiometer (biorhythm detector)

The invention claimed is:

1. A thermal stimulation apparatus for vehicles, the apparatus comprising:
    a biorhythm detector for detecting a biorhythm accompanying a periodic change in an occupant;
    a thermal stimulation generator that applies at least one thermal stimulus to the occupant; and
    a controller, operating the thermal stimulation generator with a phase difference to the biorhythm of the occupant detected by the biorhythm detector, such that the thermal stimulus to the occupant by the thermal stimulation generator is synchronized with the biorhythm of the occupant.

2. The thermal stimulation apparatus for vehicles according to claim 1, wherein:
    the biorhythm detector detects a pulse rhythm of the occupant; and
    the controller operates the thermal stimulation generator on the basis of the detection result of the biorhythm detector such that the thermal stimulus to the occupant by the thermal stimulation generator is synchronized with the pulse rhythm of the occupant.

3. The thermal stimulation apparatus for vehicles according to claim 1, wherein the thermal stimulation generator is configured so as to be capable of generating heat and absorbing heat.

4. The thermal stimulation apparatus for vehicles according to claim 1, wherein the thermal stimulation generator is provided to a vehicle seat.

5. The vehicle thermal stimulation apparatus according to claim 1, wherein the biorhythm detector detects a respiration rhythm of the occupant, and the controller operates the thermal stimulation generator on the basis of the detection result of the biorhythm detector such that the thermal stimulus is applied to the occupant by the thermal stimulation generator in synchronization with the respiration rhythm of the occupant.

6. A thermal stimulation apparatus for vehicles, the apparatus comprising:
- a biorhythm detector for detecting a biorhythm accompanying a periodic change in an occupant;
- a thermal stimulation generator, configured to contact an occupant with a heat source and move the heat source away from the occupant, the thermal stimulation generator applying thermal stimulus to the occupant; and
- a controller, operating the thermal stimulation generator on the basis of the detection result of the biorhythm detector such that the thermal stimulus to the occupant by the thermal stimulation generator is synchronized with the biorhythm of the occupant by operating the thermal stimulation generator and contacting the heat source to, and moving the heat source away from, the occupant.

7. The thermal stimulation apparatus for vehicles according to claim 6, wherein the controller operates the thermal stimulation generator synchronized with the biorhythm of the occupant detected by the biorhythm detector.

8. The vehicle thermal stimulation apparatus according to claim 6, wherein the heat source is configured so as to be capable of switching between a heat generating state and a non-heat generating state, and the controller places the heat source in the heat generating state when the heat source is contacted to the occupant, and places the heat source in the non-heat generating state when the heat source is separated from the occupant.

9. The thermal stimulation apparatus for vehicles according to claim 6, wherein the thermal stimulation generator is configured so as to be capable of generating heat and absorbing heat.

10. The thermal stimulation apparatus for vehicles according to claim 6, wherein the thermal stimulation generator is provided to a vehicle seat.

11. The vehicle thermal stimulation apparatus according to claim 6, wherein the biorhythm detector detects a respiration rhythm of the occupant, and the controller operates the thermal stimulation generator on the basis of the detection result of the biorhythm detector such that the thermal stimulus is applied to the occupant by the thermal stimulation generator in synchronization with the respiration rhythm of the occupant.

* * * * *